United States Patent
Klass et al.

(10) Patent No.: US 8,192,954 B2
(45) Date of Patent: *Jun. 5, 2012

(54) METHODS FOR ASSESSING RNA PATTERNS

(75) Inventors: Michael Klass, Oro Valley, AZ (US);
Christine Kuslich, Gilbert, AZ (US);
George Poste, Cave Creek, AZ (US)

(73) Assignee: Caris Life Sciences Luxembourg Holdings, S.A.R.L., Luxembourg (LU)

(*) Notice: Subject to any disclaimer, the term of this patent is extended or adjusted under 35 U.S.C. 154(b) by 0 days.

This patent is subject to a terminal disclaimer.

(21) Appl. No.: 12/963,468

(22) Filed: Dec. 8, 2010

(65) Prior Publication Data
US 2011/0159506 A1 Jun. 30, 2011

Related U.S. Application Data

(63) Continuation of application No. 12/609,847, filed on Oct. 30, 2009, now Pat. No. 7,888,035.

(60) Provisional application No. 61/109,742, filed on Oct. 30, 2008, provisional application No. 61/112,571, filed on Nov. 7, 2008, provisional application No. 61/114,045, filed on Nov. 12, 2008, provisional application No. 61/114,058, filed on Nov. 12, 2008, provisional application No. 61/114,065, filed on Nov. 13, 2008, provisional application No. 61/151,183, filed on Feb. 9, 2009, provisional application No. 61/250,454, filed on Oct. 9, 2009, provisional application No. 61/253,027, filed on Oct. 19, 2009, provisional application No. 61/278,049, filed on Oct. 2, 2009.

(51) Int. Cl.
*C12N 15/00* (2006.01)
*C12Q 1/68* (2006.01)
*C07K 14/00* (2006.01)

(52) U.S. Cl. ............ 435/69.1; 530/350; 435/6.12

(58) Field of Classification Search ............ None
See application file for complete search history.

(56) References Cited

U.S. PATENT DOCUMENTS

| 7,888,035 | B2 * | 2/2011 | Klass et al. | .......... 435/6.14 |
| 2006/0211000 | A1 | 9/2006 | Sorge et al. | |
| 2008/0182239 | A1 | 7/2008 | Mullinax et al. | |

FOREIGN PATENT DOCUMENTS

| WO | WO 2006/066965 A2 * | 6/2006 |
| WO | WO 2009/092386 A2 | 7/2009 |
| WO | WO 2009/092386 A3 | 7/2009 |
| WO | WO 2009/100029 A1 | 8/2009 |
| WO | WO 2010/070276 A1 | 6/2010 |

OTHER PUBLICATIONS

Porkka et al. MicroRNA expression profiling in prostate cancer. Cancer Res., vol. 67 (13), pp. 6130-6135, 2007.*
Clayton, et al. Analysis of antigen presenting cell derived exosomes, based on immuno-magnetic isolation and flow cytometry. J Immunol Methods. Jan. 1, 2001;247(1-2): 163-74.
Hemler. Tetraspanin proteins mediate cellular penetration, invasion, and fusion events and define a novel type of membrane microdomain. Annu. Rev. Cell Dev. Biol. 2003. 19:397-422.
Huber, et al. Human colorectal cancer cells induce T-cell death through release of proapoptotic microvesicles: role in immune escape. Gastroenterology. Jun. 2005; 128(7): 1796-804.
Lehman et al. Senescence-Associated Exosome Release from Human Prostate Cancer Cells. Cancer Res, 2008; 68(19):7864-71.
Llorente, et al. Caveolin-1 and MAL are located on prostasomes secreted by the prostate cancer PC-3 cell line. 2004. Journal of Cell Science 117, 5343-5351.
Piccin et al. Circulating microparticles: pathophysiology and clinical implications. Elsevier Health. 2007;21:157-171.
UK Examination report dated Nov. 24, 2011 for Application No. GB0920030.4.
UK Examination Report dated Jan. 16, 2012 for United Kingdom Patent Application No. GB0921348.9.

* cited by examiner

*Primary Examiner* — Prabha Chunduru
(74) *Attorney, Agent, or Firm* — Wilson Sonsini Goodrich & Rosati

(57) ABSTRACT

Methods and compositions for the characterizing of cancers by assessing RNA levels, such as determining an RNA pattern, are provided herein. The diagnosis, prognosis, monitoring and treatment or a cancer can be determined by detecting one or more RNAs, such as microRNAs.

24 Claims, 6 Drawing Sheets

Figure 1A

| Genes from Expression Profiling Array for 14 Prostate Cancer Samples | Frequency of Occurrence |
|---|---|
| DNMT3B | 8/14 |
| Androgen Receptor | 6/14 |
| GART | 7/14 |
| MGMT | 6/14 |
| SSTR3 | 6/14 |
| TOP2B | 9/14 |

Figure 1B

| Genes from Expression Profiling Array for 6 Prostate Cancer Samples | Frequency of Occurrence |
|---|---|
| NCAPG | 6/6 |
| CENPF | 6/6 |
| ASPM | 6/6 |
| cDNA FLJ42103 fis, clone TESOP2007041 [AK124097] | 5/6 |
| RHAMM (HMMR) | 5/6 |
| PFKFB3 | 5/6 |

Figure 1C

| Genes from IHC Analysis of 22 Prostate Cancer Samples | Frequency of Occurrence |
|---|---|
| Androgen Receptor | 18/22 |
| EGFR | 13/22 |
| HSP90 | 10/22 |
| SPARC | 10/22 |

N/A
histidine-rich glycoprotein (HRG), mRNA [NM_000412]
cDNA FLJ35379 fis, clone SKMUS2006481. [AK092698]
zinc finger protein 295
hypothetical LOC649290
amyloid P component, serum (APCS), mRNA [NM_001639]
REX1, RNA exonuclease 1 homolog (S. cerevisiae)-like 1 (REXO1L1), mRNA [NM_172239]
Q26195 PLAV1 (Q26195) Pva1 protein, partial (20%) [THC2728513]
Unknown
clone HLS IMAGE 1706664 mRNA sequence. [DQ786230]
tudor domain containing 10 (TDRD10), mRNA [NM_182499]
cDNA FLJ42103 fis, clone TESOP2007041. [AK124097]
protein disulfide isomerase family A, member 2 (PDIA2), mRNA [NM_006849]
meiosis-specific nuclear structural 1 (MNS1), mRNA [NM_018365]
acyl-Coenzyme A dehydrogenase, short/branched chain
PDZ binding kinase (PBK), mRNA [NM_018492]
NUF2, NDC80 kinetochore complex component, homolog (S. cerevisiae) (NUF2), transcript variant 1, mRNA [NM_145697]
centromere protein F, 350/400ka (mitosin) (CENPF), mRNA [NM_016343]
xr77d10.x2 NCI CGAP Ov26 cDNA clone IMAGE:2766163 3'. mRNA sequence [BE138567]
non-SMC condensin I complex, subunit G (NCAPG), mRNA [NM_022346]
similar to 3 beta-hydroxysteroid dehydrogenase/delta 5-->4-isomerase type I (3Beta-HSD I) (Trophoblast antigen FDO161G)
short-chain dehydrogenase/reductase
hyaluronan-mediated motility receptor (RHAMM) (HMMR), transcript variant 1, mRNA [NM_012484]
cDNA FLJ26031 fis, clone PNC08078. [AK129542]
ribosomal protein S15a
CN431194 328775669 GRN ES cDNA 5'. mRNA sequence [CN431194]
Zic family member 5 (odd-paired homolog, Drosophila) (ZIC5), mRNA [NM_033132]

Figure 2

| gene | GeneName | GeneSymbol | 8548log2 Ratio | 8617log2 Ratio | 8592log2 Ratio | 7419log2 Ratio | 7220log2 Ratio | 7193log2 Ratio |
|---|---|---|---|---|---|---|---|---|
| 6-phosphofructo-2-kinase/fructose-2,6-biphosphatase 3 (PFKFB3), mRNA [NM_004566] | zinc finger protein 295 | ZNF295 | 9.745432 | 6.560248 | -0.21638 | 10.1568 | 8.80924 | 8.449631 |
| hyaluronan-mediated motility receptor (RHAMM) (HMMR), transcript variant 1, mRNA [NM_012484] | | | 5.77984 | 7.429454 | 6.769025 | 8.47437 | 7.809862 | 7.837509 |
| cDNA FLJ42103 fis, clone TESOP2007041. [AK124097] | | | 8.013543 | 7.864706 | -0.008772 | 8.615137 | 7.537745 | 6.758132 |
| asp (abnormal spindle) homolog, microcephaly associated (Drosophila) (ASPM), mRNA [NM_018136] | short-chain dehydrogenase/reductase | MGC4172 | 7.292904 | 7.112278 | 7.488688 | 8.179259 | 6.649907 | 6.50685 |
| centromere protein F, 350/400ka (mitosin) (CENPF), mRNA [NM_016343] | | | 6.739871 | 6.924312 | 7.015856 | 8.499455 | 5.980858 | 6.043173 |
| non-SMC condensin I complex, subunit G (NCAPG), mRNA [NM_022346] | | | 5.742121 | 6.486546 | 7.209804 | 8.105535 | 5.880819 | 5.896208 |

| | Normal | | | | Prostate Cancer | | |
|---|---|---|---|---|---|---|---|
| Patient id | miR-141 copies | PSA | Product 141 x PSA | Patient id | miR-141 copies | PSA | Product 141 x PSA |
| 1 | 83 | 0.2 | 17 | 26 | 1503 | 1.57 | 2360 |
| 2 | 69 | 0.56 | 39 | 27 | 937 | 2.54 | 2380 |
| 3 | 113 | 0.73 | 82 | 28 | 574 | 4.66 | 2675 |
| 4 | 215 | 0.42 | 90 | 29 | 1031 | 9.17 | 9454 |
| 5 | 292 | 0.31 | 91 | 30 | 833 | 11.48 | 9563 |
| 6 | 308 | 0.35 | 108 | 31 | 476 | 45.16 | 21496 |
| 7 | 615 | 0.2 | 123 | 32 | 521 | 46.78 | 24372 |
| 8 | 145 | 0.92 | 133 | 33 | 224 | 171.8 | 38483 |
| 9 | 169 | 0.89 | 150 | 34 | 5004 | 23.04 | 115292 |
| 10 | 201 | 0.92 | 185 | 35 | 866 | 170 | 147220 |
| 11 | 603 | 0.32 | 193 | 36 | 4453 | 34 | 151402 |
| 12 | 252 | 0.86 | 217 | 37 | 761 | 215.4 | 163919 |
| 13 | 361 | 0.65 | 235 | 38 | 5505 | 37.35 | 205612 |
| 14 | 621 | 0.42 | 261 | 39 | 46125 | 38 | 1752750 |
| 15 | 417 | 0.76 | 317 | 40 | 2985 | 680.3 | 2030696 |
| 16 | 373 | 0.9 | 336 | 41 | 9309 | 345.9 | 3219983 |
| 17 | 731 | 0.5 | 366 | 42 | 7493 | 432 | 3236976 |
| 18 | 414 | 1.03 | 426 | 43 | 3404 | 963 | 3278052 |
| 19 | 468 | 0.93 | 435 | 44 | 12055 | 500 | 6027500 |
| 20 | 445 | 1.03 | 458 | 45 | 11113 | 912 | 10135056 |
| 21 | 788 | 0.68 | 536 | 46 | 11727 | 1272 | 14916744 |
| 22 | 598 | 1.08 | 646 | 47 | 20585 | 2151 | 44278335 |
| 23 | 1771 | 0.58 | 1027 | 48 | 89811 | 3647.4 | 327576641 |
| 24 | 1459 | 0.79 | 1153 | 49 | 75267 | 5974 | 449645058 |
| 25 | 2508 | 0.54 | 1354 | 50 | 78639 | 8420 | 662140380 |

Figure 5B

| miR-141 | Normals | N=25 | | | | miR-141 | PrCa | N=25 | | | |
|---|---|---|---|---|---|---|---|---|---|---|---|
| | MEAN | SDV | 95%CIM | upper | lower | | MEAN | SDV | 95%CIM | upper | lower |
| | 560.76 | 569.0021 | 223.0447 | 783.8047 | 337.7153 | | 15648.04 | 26612.09 | 10431.75 | 26079.79 | 5216.293 |
| PSA | Normals | | | | | PSA | PrCa | | | | |
| | MEAN | SDV | 95%CIM | upper | lower | | MEAN | SDV | 95%CIM | upper | lower |
| | 0.6628 | 0.271562 | 0.10645 | 0.76925 | 0.55635 | | 1044.342 | 2059.117 | 807.1591 | 1851.501 | 237.1829 |

METHODS FOR ASSESSING RNA PATTERNS

CROSS-REFERENCE

This application is a continuation of U.S. patent application Ser. No. 12/609,847, filed Oct. 30, 2009, now U.S. Pat. No. 7,888,035; which application claims the benefit of U.S. Provisional Application Nos. 61/109,742, filed Oct. 30, 2008; 61/112,571, filed Nov. 7, 2008; 61/114,045, filed Nov. 12, 2008; 61/114,058, filed Nov. 12, 2008; 61/114,065, filed Nov. 13, 2008; 61/151,183, filed Feb. 9, 2009; 61/278,049 filed Oct. 2, 2009; 61/250,454, filed Oct. 9, 2009, and 61/253,027 filed Oct. 19, 2009, each of which is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Jan. 12, 2011, is named 37901-703.301.txt and is 1 Kilobytes in size.

BACKGROUND

Patient healthcare can be greatly improved my providing improved methods of characterizing a disease or condition by providing a diagnosis, prognosis, or treatment selection for the disease or condition. The disease or condition can be detected earlier, or its stage determined to determine what type of treatment should be selected. The disease or condition can be a cancer, such as an epithelial cancer or carcinoma. There are different types of epithelial cells and these can develop into different types of cancer. For example, epithelial cells can constitute a flat surface covering of cells called squamous cells. Additionally, epithelial cells can take a glandular form called adenomatous cells. Also, epithelial cells can form a stretchy layer called transitional cells. Carcinomas make up about 85% of all cancers, and include breast, prostate, lung, colorectal, bladder and ovarian cancers.

Epithelial based cancers usually result in a solid mass or a tumor from which cancer cells migrate throughout the body eventually residing in other locations to establish secondary tumors or metastases. One of the major therapies for cancers resulting in solid tumors is the surgical removal or oblation of the tumor by physical or chemical means. After a cancer is removed from a subject, for example by surgical removal, the monitoring or detection of recurrence of the cancer at the same or secondary sites, can be indicated, so that additional therapies can be employed for treatment should that occur. Likewise, some means of monitoring the success of cancer therapy can be indicated during the treatment phase in order to determine if the therapy is being successful or not and in order to appropriately adapt the therapy accordingly.

There is a need for methods of characterizing cancers, such as epithelial cancers. For example, despite the contribution that the Prostate Specific Antigen (PSA) test has made to the management of prostate cancer, it is plagued by significant shortcomings which result from the antigen being specific for prostate tissue and not for prostate cancer. While the test is highly specific for the PSA antigen, not all prostate cancers release excessive levels of the antigen into the serum. This results in the lack of clinical sensitivity and results in frequent missing of clinically significant cancers with routine PSA examinations.

A normal PSA value is currently considered to be less than 4.0 ng/mL. It is believed that at least 20% of men with significant prostate cancers may have a PSA value less than 4.0 ng/mL. However, since PSA is made by normal, indolent hyperplastic, pre-malignant and malignant tissue, the finding of an elevated PSA (greater than 4.0 ng/mL) does not always indicate cancer. If the serum PSA is in the range of 4.0 to 10 ng/mL there is only a 25-30% chance of finding prostate cancer even through the use of repeated and more thorough biopsies (10-12 cores). The finding of an elevated PSA value frequently results in the subject undergoing an uncomfortable and potentially dangerous transrectal biopsy. It is not uncommon for a man with a significantly elevated PSA to undergo two or more biopsies, in an attempt to find the cause of the elevated serum PSA.

Thus, there is a need for improved methods for characterizing cancer. Provided herein are methods and systems that meet this need, and provides related advantages as well.

INCORPORATION BY REFERENCE

All publications and patent applications mentioned in this specification are herein incorporated by reference to the same extent as if each individual publication or patent application was specifically and individually indicated to be incorporated by reference.

SUMMARY

Provided herein are methods for characterizing a disease or condition by detecting or assessing an RNA or RNA pattern. Characterizing a condition can include diagnosing, prognosing, monitoring, selecting a treatment, or classifying a disease or condition, such as a cancer. The cancer can be an epithelial cancer, such as a breast, brain, pancreas, bone, liver, stomach, lung, colorectal, bladder, prostate or ovarian cancer. The RNA pattern can comprise detecting miRNAs, such as the expression level of miRNAs.

In some embodiments, the method includes characterizing a cancer in a subject comprising: determining a miRNA pattern in a biological sample of said subject, wherein the miRNA pattern comprises an expression level of each of a plurality of miRNAs in said sample. In some embodiments, characterizing is with increased sensitivity as compared to characterization by detecting an expression level of less than each of the plurality of miRNAs. The miRNAs can be selected from Table 1.

Also provided are methods of classifying a cancer, such as benign or malignant, and methods of determining if a solid tissue biopsy should be obtained after an initial analysis of a non-biopsy sample. The method can also further include selecting a therapy or treatment regimen based on the classification or results of the biopsy. Classifying a cancer or determining if a biopsy should be obtained can include determining the expression level of a miRNA, such as the copy number of the miRNA per microliter. The method can also include determining the expression level of PSA, such as the protein level, or a PCA3 score, which is the ratio between the PCA3 expression level and PSA expression level of a biological sample. The method can also include determining a product value to characterize a cancer. The product value can be determined by multiplying the expression level of a miRNA, such as miR-141, with the level of PSA. For example, the copy number per microliter of miRNA can be multiplied by the nanograms per microliters of PSA.

Also provided herein is a method of characterizing a cancer, such as prostate cancer, by determining the expression level of one or more miRNAs, such as miR-141, miR-629, miR-671-3p, miR-9, miR-491, miR-182, miR125a-3p, miR-324-5p, miR-148b, miR-222, or miR-370.

The RNA or RNA pattern can also be used in conjunction with other non-RNA biomarkers to characterize a cancer.

BRIEF DESCRIPTION OF THE DRAWINGS

The details of one or more exemplary embodiments are set forth in the accompanying drawings and the description below. Other features, objects, and advantages will be apparent from the description and drawings, and from the claims.

FIG. 1: illustrates the results of gene analysis of prostate cancer samples. A) In the first study, fourteen prostate cancer tissues were analyzed for gene expression profiles on the Agilent 44K Expression Profile platform. The genes with most commonly overexpressed are listed. B) In a separate study, a set of 6 prostate cancers was analyzed for the expression level of genes by using the same platform as in A). The top 100 expressing genes were identified. Those genes that listed in the top 100 for 5/6 and 6/6 of the prostate cancers are listed. C) Prostate cancer samples from 22 individuals were examined by immunohistochemistry (IHC) for the overexpression of genes. Those genes that were overexpressed in at least 10 of the 22 samples are listed.

FIG. 2 illustrates expression profiles for 6 prostate cancer samples. This figure shows the expression profile from the Agilent gene chip analysis on the 6 prostate cancer samples with the gene names listed on the right. Dark coloring or shading indicates high expression levels.

FIG. 3 illustrates analysis for cancer samples. A set of 6 prostate cancers was analyzed for the expression level of genes and the top 100 expressing genes was listed. Those genes that listed in the top 100 for 5/6 and 6/6 of the prostate cancers are listed in FIG. 1B.

FIG. 5 is a table showing the product of the PSA value and the level of miR-141 for 25 subjects with confirmed prostate cancer versus 25 subjects without prostate cancer. A) lists the miR-141 copies, the PSA levels, and product values for the prostate cancer subjects and normal subjects. B) is a table showing the mean values, standard deviation, confidence level and the upper and lower levels of miR-141 and PSA in the normal subjects and the prostate cancer subjects (PrCa).

DETAILED DESCRIPTION

Figure 4:
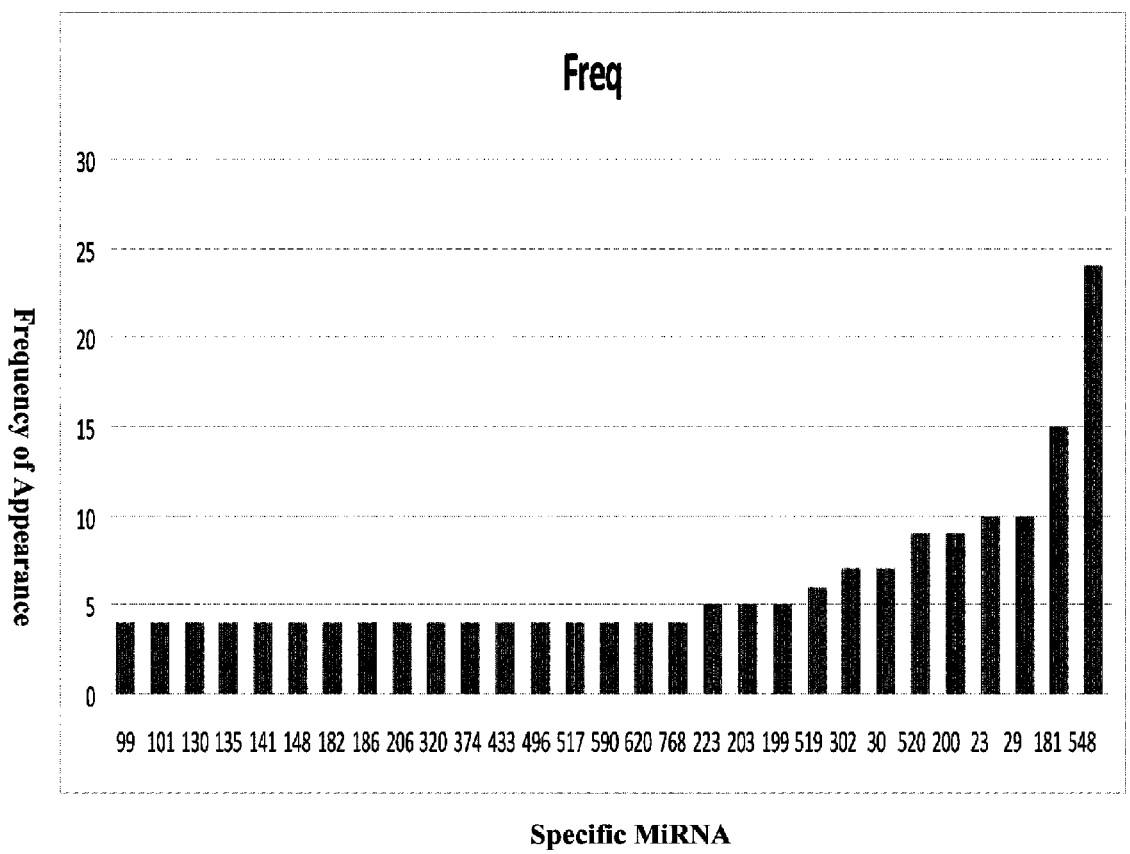
FIG. 4 is a graph illustrating the frequency of a miRNA (listed along the x-axis), by analyzing the most frequently over-expressed genes in the prostate cancer samples in a database by both immunohistochemistry (IHC) and gene expression profiling on the Agilent 44K chip, searching a publicly available miRNA database for microRNAs known to be related to those genes (for example, such as world wide web at microRNA.org), and ranking the miRNAs by frequency observed.

Provided herein are methods of characterizing a condition or disease by assessing an RNA or RNA pattern in a biological sample from a subject. Characterizing a disease or condition can include detecting, diagnosing, prognosing, or monitoring a disease or condition. Characterizing can also include detecting or diagnosing (including pre-symptomatic early stage detecting), determining the prognosis or theranosis, or determining the stage or progression of a disease or condition.

Also included is determining the drug efficacy or selecting a treatment for a disease or condition and prediction and likelihood analysis of progression of the disease or condition, such as recurrence, spread or relapse of a disease or condition based on an RNA or a plurality of RNAs, such as an RNA pattern. Characterizing a disease or condition can also include classifying the disease or condition. Furthermore, the RNA or RNA pattern determined in a sample can be used to determine whether to obtain a second sample, such as a biopsy for further analysis.

The disease or condition that can be characterized according to the methods and compositions disclosed herein can be a cancer. Examples of cancer include bladder cancer; esophageal cancer; lung cancer; stomach cancer; kidney cancer; cervical cancer; ovarian cancer; breast cancer; lymphoma; Ewing sarcoma; hematopoietic tumors; solid tumors; gastric cancer; colorectal cancer; brain cancer; epithelial cancer; nasopharyngeal cancer; uterine cancer; hepatic cancer; head-and-neck cancer; renal cancer; male germ cell tumors; malignant mesothelioma; myelodysplastic syndrome; pancreatic or biliary cancer; prostate cancer; thyroid cancer; urothelial cancer; renal cancer; Wilm's tumor; small cell lung cancer; melanoma; skin cancer; osteosarcoma; neuroblastoma; leukemia (acute lymphocytic leukemia, acute myeloid leukemia, chronic lymphocytic leukemia); glioblastoma multiforme; medulloblastoma; lymphoplasmacytoid lymphoma; or rhabdomyosarcoma. The cancer can be an epithelial cancer. Epithelial cancers are cancers of skin tissue that covers and lines the body, such as breast, brain, liver, pancreas, stomach, bone, colorectal, bladder, ovarian or lung cancer. In some embodiments, the cancer is prostate cancer.

Samples

One or more RNAs can be assessed from a biological sample obtained from a subject. The biological sample may be of any biological tissue, fluid, or cell from the subject. The sample can be solid or fluid. The sample can be a heterogeneous cell population. The sample can be sputum, blood, blood cells (e.g., white cells), a biopsy, urine, peritoneal fluid, pleural fluid, or cells derived therefrom. The biopsy can be a fine needle aspirate biopsy, a core needle biopsy, a vacuum assisted biopsy, an open surgical biopsy, a shave biopsy, a punch biopsy, an incisional biopsy, a curettage biopsy, or a deep shave biopsy. Biological samples may also include sections of tissues, such as frozen sections or formalin fixed sections taken for histological purposes. A sample can be a tumor tissue, tissue surrounding a tumor, or non-tumor tissue.

The subject can include mammals such as bovine, avian, canine, equine, feline, ovine, porcine, or primate animals (including humans and non-human primates). In some embodiments, the subject is a human of a specific gender or age. For example, the age of the subject can be at least about 30, 35, 40, 45, 50, 55, or 60 years of age. To characterize prostate cancer, the subject may be a male human of at least 50 years of age. The subject can have a pre-existing disease or condition, or a family history of a pre-existing disease or condition, such as cancer. Alternatively, the subject may not have any known pre-existing condition. The subject may also be non-responsive to an existing or past treatment, such as a treatment for cancer.

Exosomes

In some embodiments, one or more RNAs disclosed herein are assessed from exosomes of a biological sample. Exosomes are vesicles that are released into the extracellular environment from a variety of different cells such as but not limited to dendritic cells, tumor cells, lymphoid cells, mesothelial cells, epithelial cells, or cells from different tissues or organs. An exosome is created intracellularly-when a segment of the cell membrane spontaneously invaginates and is ultimately exocytosed (Keller et al., *Immunol. Lett.* 107 (2): 102-8 (2006)). Exosomes may also be referred to as microvesicles, nanovesicles, vesicles, dexosomes, blebs, prostasomes, microparticles, intralumenal vesicles, endosome-like vesicles or exocytosed vehicles.

Exosomes can also include any shed membrane bound particle that is derived from either the plasma membrane or an internal membrane. Exosomes may further include cell-derived structures bounded by a lipid bilayer membrane arising from both herniated evagination (blebbing) separation and sealing of portions of the plasma membrane or from the export of any intracellular membrane-bounded vesicular structure containing various membrane-associated proteins of cellular origin, including surface-bound molecules derived from the host circulation that bind selectively to the tumor-derived proteins together with molecules contained in the exosome lumen, including but not limited to tumor-derived microRNAs, mRNAs, and intracellular proteins. Exosomes can also include membrane fragments.

The secretion of exosomes by tumor cells and their implication in the transport of proteins and nucleic acids (e.g., microRNAs) suggest their participation in pathological processes. Exosomes have been found in a number of body fluids including but not limited to blood plasma, bronchoalveolar lavage fluid and urine, indicating relevance in vivo. Exosomes have been suggested to have a number of different functions and are believed to take part in the communication between cells, as well as transport vehicles for proteins, RNAs, DNAs, viruses, and prions.

Assessing one or more RNAs from an exosome can provide improved assay sensitivity and specificity for cancer detection, such as for the prognosis, monitoring, disease staging, and therapeutic decision-making of the cancer.

Assessing one or more RNAs to characterize a cancer can include detecting the amount of exosomes with a specific RNA or a specific RNA pattern. In other embodiments, detecting an RNA or RNA pattern of an exosome can be used to characterize a cancer. The exosome for analysis can be in a heterogeneous population of exosomes or a homogeneous, or substantially homogeneous, population of exosomes. The exosome can be purified or concentrated prior to analyzing the exosome. Exosomes may be concentrated or isolated from a biological sample using size exclusion chromatography, density gradient centrifugation, differential centrifugation, nanomembrane ultrafiltration, immunoabsorbent capture, affinity purification, microfluidic separation, or combinations thereof. For example, size exclusion chromatography such as gel permeation columns, centrifugation or density gradient centrifugation, and filtration methods can be used. For example, exosomes can be isolated by differential centrifugation, anion exchange and/or gel permeation chromatography (for example, as described in U.S. Pat. Nos. 6,899,863 and 6,812,023), sucrose density gradients, organelle electrophoresis (for example, as described in U.S. Pat. No. 7,198, 923), magnetic activated cell sorting (MACS), or with a nanomembrane ultrafiltration concentrator. Various combinations of isolation or concentration methods can be used.

Binding agents, or capture agents, can be used to isolate exosomes by binding to exosomal components. A binding or capture agent may be used after the exosomes are concentrated or isolated from a biological sample. For example, exosomes are first isolated from a biological sample before exosomes with a specific biomarker are isolated using a binding agent for the biomarker. Thus, exosomes with the specific biomarker are isolated from a heterogeneous population of exosomes. Alternatively, a binding agent may be used on a biological sample comprising exosomes without a prior isolation step of exosomes. For example, a binding agent is used to isolate exosomes with a specific biomarker from a biological sample.

The binding agent can be, but not limited to, DNA, RNA, aptamers, monoclonal antibodies, polyclonal antibodies, Fabs, Fab', single chain antibodies, synthetic antibodies, aptamers (DNA/RNA), peptoids, zDNA, peptide nucleic acids (PNAs), locked nucleic acids (LNAs), lectins, synthetic or naturally occurring chemical compounds (including but not limited to drugs, labeling reagents), or dendrimers.

In some embodiments, prostate specific exosomes, or prostatsomes, such as from a blood sample or urine is used for assessing one or more RNAs to characterize a cancer. Exosomes that are derived from a prostate cancer cells can be isolated using an antibody, or any other binding agent, for one or more antigens that are specific for a cell of prostate cancer origin such as PSA, TMPRSS2, FASLG, TNFSF10, PSMA, NGEP, Il-7RI, CSCR4, CysLT1R, TRPM8, Kv1.3, TRPV6, TRPM8, PSGR, MISIIR, galectin-3, PCA3, TMPRSS2: ERG, fragments thereof, any combination thereof, or any combination of antigens that are specific for prostate cancer cells. The binding agent can be PSA, PSMA, mAB 5D4, XPSM-A9, XPSM-A10, Galectin-3, E-selectin, Galectin-1, E4 (IgG2a kappa), or any combination thereof. The binding agent or capture agent used to isolate an exosome can also be an agent that binds exosomal "housekeeping proteins," such as CD63, CD9, CD81, or Rab-5b, or a binding agent for EpCAM is used to isolate exosomes.

RNAs

Assessment of any species of RNA can be used to characterize a disease or condition, such as cancer. The RNA can be microRNA (miRNA or miR), mRNA, small nuclear RNA, siRNA, small nucleolar RNA, or ribosomal RNA. The RNA pattern can comprise any RNA species, such as a microRNA (miRNA or miR), mRNA, small nuclear RNA, small nucleolar RNA, ribosomal RNA, or any combination thereof. The RNA pattern can comprise a single species of RNA or any combination of species, such as a miRNA and a mRNA. The assessment of an RNA can include determining or detecting the expression level of an RNA, such as the overexpression or underexpression as compared to a control, the absence or presence of an RNA, or the copy number of the RNA, such as copy numbers per microliter of sample, such as the copy number per microliter of plasma, or the copy number per microliter of serum. In some embodiments, assessing an RNA is detecting or determining the sequence of an RNA, or detecting a mutation or variant of an RNA.

A plurality of RNAs can be used to characterize a disease or condition, such as cancer. For example, an RNA pattern can comprise 2 or more different RNAs, such as at least 2, 3, 4, 5, 6, 7, 8, 9, 10, 15, 20, 25, 30, 40, 50, 60, 70, 80, 90, 100, 1000, 2500, 5000, 7500, 10,000, 100,000, 150,000, 200,000, 250,000, 300,000, 350,000, 400,000, 450,000, 500,000, 750, 000, or 1,000,000 different RNAs. In some embodiments, the RNA pattern comprises at least 2, 3, 4, 5, 6, 7, 8, 9, 10, 15, 20, 25, 30, 40, 50, 60, 70, 80, 90, 100, 1000, 2500, 5000, 7500, 10,000, 100,000, 150,000, 200,000, 250,000, 300,000, 350, 000, 400,000, 450,000, 500,000, 750,000, or 1,000,000 different miRNAs. The RNA pattern can also comprise one or more different miRNAs in combination with other species of RNAs, such as mRNA.

Also provided herein are methods of assessing one or more RNAs that can be used to diagnose a cancer. Diagnosis can include a negative diagnosis, such as no cancer is present. In other embodiments, diagnosis may include identifying the stage of a cancer, or the pre-symptomatic stages of a cancer.

The one or more RNAs can also be used to provide a prognosis of a cancer, such as providing the risk or susceptibility of having a cancer or the aggressiveness or malignancy of a cancer.

Assessing one or more RNAs in sample can also be used to select a cancer therapy. Detection of one or more RNAs can be used to determine the efficacy of a cancer therapy or treatment, such as the relative improvement or deterioration of the subject's condition. Assessing one or more RNAs from samples of patients treated with effective therapies or non-effective therapies can be determined and used as a reference for selecting a therapy for a subject. In another embodiment, as a subject's cancer becomes progressively worse or better, the level of one or more RNAs may change, and compared to a reference of one or more RNAs from patients that were in a worse or better stage of the cancer.

The treatment or therapeutic selected based on one or more RNAs can be a treatment for cancer, such as an anti-cancer regimen or treatment that is selected from one or more of the following: vaccination, anti-growth factor or signal transduction therapy, radiotherapy, endocrine therapy, or human antibody therapy chemotherapy. The treatment can comprise a DNA damaging agent, topoisomerase inhibitor, mitotic inhibitor or a combination thereof. Many chemotherapeutics are presently known in the art and can be used in combination with the one or more compounds described herein. For example, the chemotherapeutic can be selected from the group consisting of: a mitotic inhibitor, alkylating agent, antimetabolite, intercalating antibiotic, growth factor inhibitor, cell cycle inhibitor, enzyme, topoisomerase inhibitor, biological response modifier, anti-hormone, angiogenesis inhibitor, and anti-androgen. As used herein, cancer treatment, cancer therapy and the like encompasses treatments such as surgery, such as cutting, abrading, ablating (by physical or chemical means, or a combination of physical or chemical means), suturing, lasering or otherwise physically changing body tissues and organs), radiation therapy, administration of chemotherapeutic agents and combinations of any two or all of these methods. Combination treatments may occur sequentially or concurrently. Treatments, such as radiation therapy and/or chemotherapy, that are administered prior to surgery, are referred to as neoadjuvant therapy. Treatments, such as radiation therapy and/or chemotherapy, administered after surgery is referred to herein as adjuvant therapy. Examples of surgeries that may be used for prostate cancer treatment include, but are not limited to radical prostatectomy, cryotherapy, transurethral resection of the prostate, and the like.

Detection of one or more RNAs can also be used to determine the efficacy of a cancer therapy or treatment, such as the relative improvement or deterioration of the subject's condition. One or more RNAs for patients being treated for cancer can be determined and correlated to the improvement or beneficial efficacy, which is then used as a reference. For example, the improvement or beneficial efficacy can typically be assessed by determining if one or more of the following events has occurred: decreased or tumor size, decreased or tumor cell proliferation, decreased or numbers of cells, decreased or neovascularization and/or increased apoptosis. One or more of these occurrences may, in some cases, result in partial or total elimination of the cancer and prolongation of survival of the subject. Alternatively, for terminal stage cancers, treatment may result in stasis of disease, better quality of life and/or prolongation of survival. The converse result and/or stasis in any of those events can indicate inefficacy of treatment or therapy. Other methods of assessing treatment are known in the art and contemplated herein. Different assessments can be correlated with different RNAs or RNA patterns.

Assessing one or more RNAs can also be used monitor the progress of an anti-cancer treatment regimen or treatment in a subject, or the recurrence of a cancer. For example, the RNA or RNA patterns at various timepoint throughout a treatment. The RNA or RNA pattern can also be used to monitor a subject for the spread of a cancer. For example, miR-141 can be used for detecting the recurrence of colorectal cancer. Currently, colorectal cancer recurrence is measured by the level of the antigen CEA (carcino embryonic antigen). However, CEA can have confounding issues when used alone. For example, not all metastatic colorectal tumors express CEA, creating the need for additional markers, like miR-141. Similar issues are known for other single antigen tests for epithelial based cancers such as ovarian, breast, lung and bladder cancer.

Recurrence can be determined by periodically obtaining sample from a subject and monitoring the RNA or RNA pattern periodically from a sample of the subject. For example, an epithelial cancer has recurred if the miR-141 in the periodic blood samples shows a steady change in amount or is significantly elevated when compared to a miR-141 amount in a control sample that corresponds to subjects without epithelial cancer. In one embodiment, after a cancer is removed from a subject, for example surgically, the subject is monitored and through assessing an RNA or RNA pattern, the recurrence of the cancer at the same or secondary site can be identified so that additional therapies can be employed for treatment. In another embodiment, a subject is monitored during the treatment phase by having samples taken before and during treatment for analysis of an RNA or RNA pattern. Based on the RNA or RNA pattern, the therapy can be determined successful or not, if the therapy should be adapted or if the patient should try another therapy.

Classification

In another embodiment, assessing one or more RNAs can be used to classify or stage a cancer. The classification and staging may also be used to assess treatment of cancers.

For example, the cancer can be classified based on the TNM classification of malignant tumors. This cancer staging system can be used to describe the extent of cancer in a subject's body. T describes the size of the tumor and whether it has invaded nearby tissue, N describes regional lymph nodes that are involved, and M describes distant metastasis. TNM is maintained by the International Union Against Cancer (UICC) and is used by the American Joint Committee on Cancer (AJCC) and the International Federation of Gynecology and Obstetrics (FIGO). One would understand that not all tumors have TNM classifications such as, for example, brain tumors. Generally, T (a,is,(0), 1-4) is measured as the size or direct extent of the primary tumor. N (0-3) refers to the degree of spread to regional lymph nodes: N0 means that tumor cells are absent from regional lymph nodes, N1 means that tumor cells spread to the closest or small numbers of regional lymph nodes, N2 means that tumor cells spread to an extent between N1 and N3; N3 means that tumor cells spread to most distant or numerous regional lymph nodes. M (0/1) refers to the presence of metastasis: M0 means that no distant metastasis are present; M1 means that metastasis has occurred to distant organs (beyond regional lymph nodes). Other parameters may also be assessed. G (1-4) refers to the grade of cancer cells (i.e., they are low grade if they appear similar to normal cells, and high grade if they appear poorly differentiated). R (0/1/2) refers to the completeness of an operation (i.e., resection-boundaries free of cancer cells or not). L (0/1) refers to invasion into lymphatic vessels. V (0/1) refers to invasion into vein. C (1-4) refers to a modifier of the certainty (quality) of V.

The methods also include classifying a prostate tumor based on the Gleason scoring system. The Gleason scoring system is based on microscopic tumor patterns assessed by a pathologist while interpreting the biopsy specimen. When prostate cancer is present in the biopsy, the Gleason score is based upon the degree of loss of the normal glandular tissue architecture (i.e. shape, size and differentiation of the glands). The classic Gleason scoring system has five basic tissue patterns that are technically referred to as tumor "grades." The microscopic determination of this loss of normal glandular structure caused by the cancer is represented by a grade, a number ranging from 1 to 5, with 5 being the worst grade. Grade 1 is typically where the cancerous prostate closely resembles normal prostate tissue. The glands are small, well-formed, and closely packed. At Grade 2 the tissue still has well-formed glands, but they are larger and have more tissue between them, whereas at Grade 3 the tissue still has recognizable glands, but the cells are darker. At high magnification, some of these cells in a Grade 3 sample have left the glands and are beginning to invade the surrounding tissue. Grade 4 samples have tissue with few recognizable glands and many cells are invading the surrounding tissue. For Grade 5 samples, the tissue does not have recognizable glands, and are often sheets of cells throughout the surrounding tissue.

For example, after an initial analysis of a biological sample for one or more RNAs, based on the levels of one or more RNAs, a second analysis can be performed by a pathologist, where the pathologist determines a Gleason score for the sample. A biological fluid, such as urine can be analyzed for one or more RNAs prior to obtaining a biopsy to determine a Gleason score for a subject.

Assessing one or more RNAs can also be used to classify a cancer as malignant (e.g., aggressive) or benign (e.g., indolent). For example, a miRNA pattern can be determined for a biological sample and used to classify whether a cancer is aggressive or indolent. For example, the methods disclosed herein can be used to classify prostate cancer, by distinguishing between benign (e.g., indolent) and malignant (e.g., aggressive) prostate cancers.

Classification can be based on the amount or level of an RNA, or on the level of each of a plurality of RNAs. For example, the classification for a cancer is indolent epithelial cancer when the level of an RNAs, such as miRNA, is less than about 3000 copies per microliter of sample, for example, a serum sample. The classification for a cancer can be benign if the RNA level is between about 1000 and about 3000 copies per microliter, such as less than about 1100, 1200, 1300, 1400, 1500, 1600, 1700, 1800, 1900, 2000, 2100, 2200, 2300, 2400, 2500, 2600, 2700, 2800, 2900 or 3000. In some embodiments, a cancer is classified as benign when the expression level of a subset of RNAs that are detected is less than about 3000 copies per microliter of sample. In other embodiments, a cancer is classified as benign when the expression level of a subset of RNAs that are detected is between about 1000 and about 3000 copies per microliter of sample, such as less than about 1100, 1200, 1300, 1400, 1500, 1600, 1700, 1800, 1900, 2000, 2100, 2200, 2300, 2400, 2500, 2600, 2700, 2800, 2900 or 3000 copies per microliter.

In some embodiments, the classification of an epithelial cancer, such as prostate cancer, is malignant when the level of the RNA, such as miRNA, is at least about 9000, such as between about 9000 and about 26000 copies per microliter of sample, such as serum sample. For example, if the sample has at least about 9100, 9200, 9300, 9400, 9500, 9600, 9700, 9800, 9900, 10000, 10100, 10200, 10300, 10400, 10500, 10600, 10700, 10800, 10900, 11000, 11100, 11200, 11300, 11400, 11500, 11600, 11700, 11800, 11900, 12000, 12100, 12200, 12300, 12400, 12500, 13000, 13500, 14000, 14500, 15000, 15500, 16000, 16500, 17000, 17500, 18000, 18500, 19000, 19500, 20000, 20500, 21000, 21500, 22000, 22500, 23000, 23500, 24000, 24500, 25000, or 25,500 copies per microliter.

Additional Biological Samples

The assessment of one or more RNAs can be performed on a sample obtained non-invasively, such as a urine sample or blood sample, to characterize a disease or condition, such as cancer. This can reduce the number of unnecessary biopsies or other invasive procedures for a subject. Thus, in some embodiments, assessing one or more RNAs is performed on a first sample from a subject. Based on the assessment of the one or more RNAs performed on the first sample, a second sample from the subject can be obtained for analysis to characterize a cancer. For example, the second sample can be of a different sample type from the first sample type and used for a different type of analysis, such as for histological examination, such as immunohistochemistry (IHC), in situ hybridization (such as fluorescent in situ hybridization), PCR, real-time PCR, microarray analysis or sequencing.

The first sample can be obtained in a less intrusive or less invasive method than is the second sample. For example, the first sample can be urine or blood, and the second sample can be a biopsy. For example, the first sample can be a blood sample that is used to assess one or more RNAs, and depending on the level of RNAs, a biopsy for histological examination can be obtained to characterize the cancer, such as diagnose the presence or absence of cancerous tissue or the stage of a cancer.

For example, if an RNA level in a first sample is between about 1500 to about 9000 copies per microliter, such as at least about 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, or 8900, a second sample, such as a biopsy or tissue sample for histological examination is taken from the subject. In some embodiments, if the level is between about 1500 to about 4500 copies per microliter, a second sample is taken from the subject. In yet other embodiments, a second sample is not obtained from a subject if the level of the RNA, such as a miRNA, is less than about 1500 copies per microliter, such as less than about 1100, 1200, 1300, 1400, or 1500.

In some embodiments, assessing one or more RNAs is used to determine the need for a second or third sample, such as a second or third biopsy. For example, after an initial elevated serum miR-141 is observed followed by a negative biopsy or a negative second biopsy. Such method includes the steps of obtaining a blood sample from a subject and determining an amount of miR-141 in serum of the subject's blood sample, and a biopsy is indicated when serum miR-141 is significantly different from a miR-141 amount in a control sample that corresponds to subjects without epithelial cancer, or to a previous determination of the same patient's miR-141 levels, any significant increase in miR-141 level indicating the need for another biopsy.

Sensitivity and Specificity

The methods and compositions disclosed herein can also provide increased sensitivity and the specificity for characterizing cancers, such as for detecting, diagnosing, prognosing, or monitoring for cancer recurrence and therapeutic efficacy are provided herein.

The sensitivity can be determined by: (number of true positives)/(number of true positives+number of false negatives). The specificity can be determined by: (number of true negatives)/(number of true negatives+number of false positives).

Assessing one or more RNAs disclosed herein can be used to characterize a cancer with at least about 70% or 75% specificity. For example, a cancer can be characterized with greater than about 76, 77, 78, 79, 80, 81, 82, 83, 84, 85, 86, 87, 88, 89, 90, 91, 92, 93, 94, 95, 96, or 97% specificity. The cancer can be characterized with at least about 97.1, 97.2, 97.3, 97.4, 97.5, 97.6, 97.7, 97.8, 97.8, 97.9, 98.0, 98.1, 98.2, 98.3, 98.4, 98.5, 98.6, 98.7, 98.8, 98.9, 99.0, 99.1, 998.2, 99.3, 99.4, 99.5, 99.6, 99.7, 99.8, 99.9% specificity. In yet other embodiments, the cancer can be characterized with 100% specificity.

In some embodiments, the cancer can be characterized with at least about 60% sensitivity, such as at least about 60, 65, 70, 75, 80, 81, 82, 83, 84, 85, 86, 87, 88, 89, 90, 91, 92, 93, 94, 95, 96, or 97% sensitivity. The cancer can be characterized with at least about 97.1, 97.2, 97.3, 97.4, 97.5, 97.6, 97.7, 97.8, 97.8, 97.9, 98.0, 98.1, 98.2, 98.3, 98.4, 98.5, 98.6, 98.7, 98.8, 98.9, 99.0, 99.1, 99.2, 99.3, 99.4, 99.5, 99.6, 99.7, 99.8, 99.9% sensitivity. In yet other embodiments, the cancer can be characterized with 100% sensitivity.

In some embodiments, assessing a plurality of RNAs provides increased specificity or sensitivity in the characterization of cancer as compared to assessing less than the plurality of RNAs. For example, the sensitivity or specificity may be at increased by at least about 5, 10, 15, 20, 30, 35, 40, 50, 75, 100, 150, 200, 250, 500, 1000% or more than detection with less than the plurality of RNAs. For example, the sensitivity for characterizing a cancer is 50% using one RNA, whereas using an additional RNA provides an increased sensitivity of 60%, an increase of 20%. Thus, in some embodiments, the number of RNAs analyzed is the number such that an increase in the number provides increased sensitivity or specificity. In some embodiments, assessing at least 2, 3, 4, 5, 6, 7, 8, 9, 10, 15, 20, 25, 30, 40, 50, 60, 70, 80, 90, 100, 1000, 2500, 5000, 7500, 10,000, 100,000, 150,000, 200,000, 250,000, 300,000, 350,000, 400,000, 450,000, 500,000, 750,000, or 1,000,000 RNAs provide increased specificity or sensitivity in the characterization of a cancer, as compared to less than the number of RNAs assessed. For example, assessing at least 2 RNAs, such as at least two miRNAs, can provide increased specificity or sensitivity in the characterization of cancer as compared to assessing one of the two miRNAs.

MicroRNAs

The one or more RNAs assessed herein can comprise one or more microRNAs (miRNAs, miRs). MiRNAs are short RNA strands approximately 21-23 nucleotides in length. MiRNAs are encoded by genes that are transcribed from DNA but not translated into protein (non-coding RNA). Instead they are processed from primary transcripts known as pri-miRNA to short stem-loop structures called pre-miRNA and finally to functional miRNA, as the precursors typically form structures that fold back on each other in self-complementary regions. They are then processed by the nuclease Dicer in animals or DCL1 in plants. Mature miRNA molecules are partially complementary to one or more messenger RNA (mRNA) molecules. The sequences of miRNA can be accessed at publicly available databases, such as world wide web at microRNA.org or world wide web at mirz.unibas.cb/cgi/miRNA.cgi.

A number of miRNAs are involved in gene regulation, and miRNAs are part of a growing class of non-coding RNAs that is now recognized as a major tier of gene control. In some cases, miRNAs can interrupt translation by binding to regulatory sites embedded in the 3'-UTRs of their target mRNAs, leading to the repression of translation. Target recognition involves complementary base pairing of the target site with the miRNA's seed region (positions 2-8 at the miRNA's 5' end), although the exact extent of seed complementarity is not precisely determined and can be modified by 3' pairing. In other cases, miRNAs function like small interfering RNAs (siRNA) and bind to perfectly complementary mRNA sequences to destroy the target transcript.

Characterization of a number of miRNAs indicates that they influence a variety of processes, including early development, cell proliferation and cell death, apoptosis and fat metabolism. For example, some miRNAs, such as lin-4, let-7, mir-14, mir-23, and bantam, have been shown to play critical roles in cell differentiation and tissue development. Others are believed to have similarly important roles because of their differential spatial and temporal expression patterns.

In some embodiments, a single miRNA is assessed to characterize a cancer. In yet other embodiments, at least 2, 3, 4, 5, 6, 7, 8, 9, 10, 15, 20, 25, 30, 40, 50, 60, 70, 80, 90, 100, 1000, 2500, 5000, 7500, 10,000, 100,000, 150,000, 200,000, 250,000, 300,000, 350,000, 400,000, 450,000, 500,000, 750,000, or 1,000,000 miRNAs are assessed. In some embodiments, 1 or more miRNAs is assessed in combination with other species of RNAs, such as mRNA, to characterize a cancer.

In some embodiments, the miRNAs are used to detect prostate cancer. For example, the level of a microRNA that is detectable in sample can be indicative of prostate cancer and levels that are not detectable are not indicative of prostate cancer. In some embodiments, detection of 1, 2, 3, 4, 5, 6, 7, 8, 9, 10, 15, 20, 25, 30, 40, 50, 60, 70, 80, 90, 100, 1000, 2500, 5000, 7500, 10,000, 100,000, 150,000, 200,000, 250,000, 300,000, 350,000, 400,000, 450,000, 500,000, 750,000, 1,000,000 or more miRNAs is used to detect prostate cancer. A change in the expression level, such as absence, presence, underexpression or overexpression of the miRNA as compared to a reference level, such as a level determined for a subject without the cancer (such as age and sex controlled), can be used to characterize a cancer for the subject.

For example, a reference level for classifying a prostate cancer as benign or malignant can include obtaining a blood sample from a subject, determining an amount of a miRNA in the subject's blood sample, and comparing the amount of the miRNA to one or more controls having benign prostate cancer or malignant prostate cancer. The step of comparing the amount of the miRNA to one or more controls may include the steps of obtaining a range of the miRNA found in the blood for a plurality of subjects having benign prostate cancer to arrive at a first control range, obtaining a range of the miRNA found in the blood for a plurality of subjects having malignant prostate cancer to arrive at a second control range, and comparing the amount of the miRNA in the subject's blood sample with the first and second control ranges to determine if the subject's prostate cancer is classified as benign prostate cancer or malignant prostate cancer.

MiR-200 Family

In some embodiments, the miRNA is a member of the miR-200 family. The miR-200 family is believed to determine the epithelial phenotype of cancer cells by targeting the E-cadherin repressors ZEB1 and ZEB2. The miR-200 family includes miR-141, miR-236, miR-200a, mir-200b, mir-200c and mir-429. In some embodiments more than one miR-200 family member is analyzed to detect an epithelial cancer.

For example, miR-141 can be obtained from blood (serum or plasma) and correlated with the occurrence of metastatic epithelial cancer. MiR-141 can be used to detect cancer recurrence and therapeutic efficacy for epithelial based cancers, such as prostate cancer, including the use of miR-141 to monitor subjects who have undergone surgical removal of their cancer. For example, currently subjects are monitored with other markers like serum PSA for prostate cancer. A steady rise in serum PSA would indicate a recurrence and spread of the cancer. However, many prostate cancer metastases do not express PSA and are therefore missed by this monitoring method. By the time the cancer has been detected it has often spread beyond any treatment options. Other epithelial cancers have similar issues regarding current diagnostic regimens.

Gene Associated MiRNAs

The miRNA can also be a miRNA that interacts with the mRNA of PFKFB3, RHAMM (HMMR), cDNA FLJ42103, ASPM, CENPF, NCAPG, Androgen Receptor, EGFR, HSP90, SPARC, DNMT3B, GART, MGMT, SSTR3, or TOP2B. For example, such as the microRNAs that can be detected, and the gene with which they are associated as listed in Table 1. The miRs can be used to characterize an epithelial cancer, such as prostate cancer.

TABLE 1

Gene Name and Their Associated miRNAs

| Gene | miRNA Associated with Gene |
|---|---|
| Androgen receptor | hsa-miR-124a |
| | hsa-miR-130a |
| | hsa-miR-130b |
| | hsa-miR-143 |
| | hsa-miR-149 |
| | hsa-miR-194 |
| | hsa-miR-29b |
| | hsa-miR-29c |
| | hsa-miR-301 |
| | hsa-miR-30a-5p |
| | hsa-miR-30d |
| | hsa-miR-30e-5p |
| | hsa-miR-337 |
| | hsa-miR-342 |
| | hsa-miR-368 |
| | hsa-miR-488 |
| | hsa-miR-493-5p |
| | hsa-miR-506 |
| | hsa-miR-512-5p |
| | hsa-miR-644 |
| | hsa-miR-768-5p |
| | hsa-miR-801 |
| DNMT3B | hsa-miR-618 |
| | hsa-miR-1253 |
| | hsa-miR-765 |
| | hsa-miR-561 |
| | hsa-miR-330-5p |
| | hsa-miR-326 |
| | hsa-miR-188 |
| | hsa-miR-203 |
| | hsa-miR-221 |
| | hsa-miR-222 |
| | hsa-miR-26a |
| | hsa-miR-26b |
| | hsa-miR-29a |
| | hsa-miR-29a |
| | hsa-miR-29b |
| | hsa-miR-29c |
| | hsa-miR-370 |
| | hsa-miR-379 |
| | hsa-miR-429 |
| | hsa-miR-519e* |
| | hsa-miR-598 |
| | hsa-miR-618 |
| | hsa-miR-635 |

TABLE 1-continued

Gene Name and Their Associated miRNAs

| Gene | miRNA Associated with Gene |
|---|---|
| GART | hsa-miR-101 |
| | hsa-miR-101 |
| | hsa-miR-141 |
| | hsa-miR-144 |
| | hsa-miR-182 |
| | hsa-miR-189 |
| | hsa-miR-199a |
| | hsa-miR-199b |
| | hsa-miR-200a |
| | hsa-miR-200b |
| | hsa-miR-202 |
| | hsa-miR-203 |
| | hsa-miR-223 |
| | hsa-miR-329 |
| | hsa-miR-383 |
| | hsa-miR-429 |
| | hsa-miR-433 |
| | hsa-miR-485-5p |
| | hsa-miR-493-5p |
| | hsa-miR-499 |
| | hsa-miR-519a |
| | hsa-miR-519b |
| | hsa-miR-519c |
| | hsa-miR-569 |
| | hsa-miR-591 |
| | hsa-miR-607 |
| | hsa-miR-627 |
| | hsa-miR-635 |
| | hsa-miR-659 |
| MGMT | hsa-miR-122a |
| | hsa-miR-142-3p |
| | hsa-miR-17-3p |
| | hsa-miR-181a |
| | hsa-miR-181b |
| | hsa-miR-181c |
| | hsa-miR-181d |
| | hsa-miR-199b |
| | hsa-miR-200a* |
| | hsa-miR-217 |
| | hsa-miR-302b* |
| | hsa-miR-32 |
| | hsa-miR-324-3p |
| | hsa-miR-34a |
| | hsa-miR-371 |
| | hsa-miR-425-5p |
| | hsa-miR-496 |
| | hsa-miR-514 |
| | hsa-miR-515-3p |
| | hsa-miR-516-3p |
| | hsa-miR-574 |
| | hsa-miR-597 |
| | hsa-miR-603 |
| | hsa-miR-653 |
| | hsa-miR-655 |
| | hsa-miR-92 |
| | hsa-miR-92b |
| | hsa-miR-99a |
| Top2B | hsa-miR-548f |
| | hsa-miR-548a-3p |
| | hsa-miR-548g |
| | hsa-miR-513a-3p |
| | hsa-miR-548c-3p |
| | hsa-miR-101 |
| | hsa-miR-653 |
| | hsa-miR-548d-3p |
| | hsa-miR-575 |
| | hsa-miR-297 |
| | hsa-miR-576-3p |
| | hsa-miR-548b-3p |
| | hsa-miR-624 |
| | hsa-miR-548n |
| | hsa-miR-758 |
| | hsa-miR-1253 |
| | hsa-miR-1324 |
| | hsa-miR-23b |
| | hsa-miR-320a |

TABLE 1-continued

Gene Name and Their Associated miRNAs

| Gene | miRNA Associated with Gene |
|---|---|
| | hsa-miR-320b |
| | hsa-miR-1183 |
| | hsa-miR-1244 |
| | hsa-miR-23a |
| | hsa-miR-451 |
| | hsa-miR-568 |
| | hsa-miR-1276 |
| | hsa-miR-548e |
| | hsa-miR-590-3p |
| | hsa-miR-1 |
| | hsa-miR-101 |
| | hsa-miR-126 |
| | hsa-miR-126* |
| | hsa-miR-129 |
| | hsa-miR-136 |
| | hsa-miR-140 |
| | hsa-miR-141 |
| | hsa-miR-144 |
| | hsa-miR-147 |
| | hsa-miR-149 |
| | hsa-miR-18 |
| | hsa-miR-181b |
| | hsa-miR-181c |
| | hsa-miR-182 |
| | hsa-miR-184 |
| | hsa-miR-186 |
| | hsa-miR-189 |
| | hsa-miR-191 |
| | hsa-miR-19a |
| | hsa-miR-19b |
| | hsa-miR-200a |
| | hsa-miR-206 |
| | hsa-miR-210 |
| | hsa-miR-218 |
| | hsa-miR-223 |
| | hsa-miR-23a |
| | hsa-miR-23b |
| | hsa-miR-24 |
| | hsa-miR-27a |
| | hsa-miR-302 |
| | hsa-miR-30a |
| | hsa-miR-31 |
| | hsa-miR-320 |
| | hsa-miR-323 |
| | hsa-miR-362 |
| | hsa-miR-374 |
| | hsa-miR-383 |
| | hsa-miR-409-3p |
| | hsa-miR-451 |
| | hsa-miR-489 |
| | hsa-miR-493-3p |
| | hsa-miR-514 |
| | hsa-miR-542-3p |
| | hsa-miR-544 |
| | hsa-miR-548a |
| | hsa-miR-548b |
| | hsa-miR-548c |
| | hsa-miR-548d |
| | hsa-miR-559 |
| | hsa-miR-568 |
| | hsa-miR-575 |
| | hsa-miR-579 |
| | hsa-miR-585 |
| | hsa-miR-591 |
| | hsa-miR-598 |
| | hsa-miR-613 |
| | hsa-miR-649 |
| | hsa-miR-651 |
| | hsa-miR-758 |
| | hsa-miR-768-3p |
| | hsa-miR-9* |
| HSP90 | hsa-miR-1 |
| | hsa-miR-513a-3p |
| | hsa-miR-548d-3p |
| | hsa-miR-642 |
| | hsa-miR-206 |
| | hsa-miR-450b-3p |
| | hsa-miR-152 |
| | hsa-miR-148a |
| | hsa-miR-148b |
| | hsa-miR-188-3p |
| | hsa-miR-23a |
| | hsa-miR-23b |
| | hsa-miR-578 |
| | hsa-miR-653 |
| | hsa-miR-1206 |
| | hsa-miR-192 |
| | hsa-miR-215 |
| | hsa-miR-181b |
| | hsa-miR-181d |
| | hsa-miR-223 |
| | hsa-miR-613 |
| | hsa-miR-769-3p |
| | hsa-miR-99a |
| | hsa-miR-100 |
| | hsa-miR-454 |
| | hsa-miR-548n |
| | hsa-miR-640 |
| | hsa-miR-99b |
| | hsa-miR-150 |
| | hsa-miR-181a |
| | hsa-miR-181c |
| | hsa-miR-522 |
| | hsa-miR-624 |
| | hsa-miR-1 |
| | hsa-miR-130a |
| | hsa-miR-130b |
| | hsa-miR-146 |
| | hsa-miR-148a |
| | hsa-miR-148b |
| | hsa-miR-152 |
| | hsa-miR-181a |
| | hsa-miR-181b |
| | hsa-miR-181c |
| | hsa-miR-204 |
| | hsa-miR-206 |
| | hsa-miR-211 |
| | hsa-miR-212 |
| | hsa-miR-215 |
| | hsa-miR-223 |
| | hsa-miR-23a |
| | hsa-miR-23b |
| | hsa-miR-301 |
| | hsa-miR-31 |
| | hsa-miR-325 |
| | hsa-miR-363* |
| | hsa-miR-566 |
| | hsa-miR-9 |
| | hsa-miR-99b |
| ASPM | hsa-miR-1 |
| | hsa-miR-122a |
| | hsa-miR-135a |
| | hsa-miR-135b |
| | hsa-miR-137 |
| | hsa-miR-153 |
| | hsa-miR-190 |
| | hsa-miR-206 |
| | hsa-miR-320 |
| | hsa-miR-380-3p |
| | hsa-miR-382 |
| | hsa-miR-433 |
| | hsa-miR-453 |
| | hsa-miR-493-5p |
| | hsa-miR-496 |
| | hsa-miR-499 |
| | hsa-miR-507 |
| | hsa-miR-517b |
| | hsa-miR-548a |
| | hsa-miR-548c |
| | hsa-miR-567 |
| | hsa-miR-568 |
| | hsa-miR-580 |

TABLE 1-continued

Gene Name and Their Associated miRNAs

| Gene | miRNA Associated with Gene |
|---|---|
| SPARC | hsa-miR-602 |
| | hsa-miR-651 |
| | hsa-miR-653 |
| | hsa-miR-758 |
| | hsa-miR-9* |
| | hsa-miR-768-5p |
| | hsa-miR-203 |
| | hsa-miR-196a |
| | hsa-miR-569 |
| | hsa-miR-187 |
| | hsa-miR-641 |
| | hsa-miR-1275 |
| | hsa-miR-432 |
| | hsa-miR-622 |
| | hsa-miR-296-3p |
| | hsa-miR-646 |
| | hsa-miR-196b |
| | hsa-miR-499-5p |
| | hsa-miR-590-5p |
| | hsa-miR-495 |
| | hsa-miR-625 |
| | hsa-miR-1244 |
| | hsa-miR-512-5p |
| | hsa-miR-1206 |
| | hsa-miR-1303 |
| | hsa-miR-186 |
| | hsa-miR-302d |
| | hsa-miR-494 |
| | hsa-miR-562 |
| | hsa-miR-573 |
| | hsa-miR-10a |
| | hsa-miR-203 |
| | hsa-miR-204 |
| | hsa-miR-211 |
| | hsa-miR-29a |
| | hsa-miR-29b |
| | hsa-miR-29c |
| | hsa-miR-29c |
| | hsa-miR-339 |
| | hsa-miR-433 |
| | hsa-miR-452 |
| | hsa-miR-515-5p |
| | hsa-miR-517a |
| | hsa-miR-517b |
| | hsa-miR-517c |
| | hsa-miR-592 |
| | hsa-miR-96 |
| PFKB3 | hsa-miR-513a-3p |
| | hsa-miR-1286 |
| | hsa-miR-488 |
| | hsa-miR-539 |
| | hsa-miR-658 |
| | hsa-miR-524-5p |
| | hsa-miR-1258 |
| | hsa-miR-150 |
| | hsa-miR-216b |
| | hsa-miR-377 |
| | hsa-miR-135a |
| | hsa-miR-26a |
| | hsa-miR-548a-5p |
| | hsa-miR-26b |
| | hsa-miR-520d-5p |
| | hsa-miR-224 |
| | hsa-miR-1297 |
| | hsa-miR-1197 |
| | hsa-miR-182 |
| | hsa-miR-452 |
| | hsa-miR-509-3-5p |
| | hsa-miR-548m |
| | hsa-miR-625 |
| | hsa-miR-509-5p |
| | hsa-miR-1266 |
| | hsa-miR-135b |
| | hsa-miR-190b |
| | hsa-miR-496 |
| | hsa-miR-616 |

TABLE 1-continued

Gene Name and Their Associated miRNAs

| Gene | miRNA Associated with Gene |
|---|---|
| | hsa-miR-621 |
| | hsa-miR-650 |
| | hsa-miR-105 |
| | hsa-miR-19a |
| | hsa-miR-346 |
| | hsa-miR-620 |
| | hsa-miR-637 |
| | hsa-miR-651 |
| | hsa-miR-1283 |
| | hsa-miR-590-3p |
| | hsa-miR-942 |
| | hsa-miR-1185 |
| | hsa-miR-577 |
| | hsa-miR-602 |
| | hsa-miR-1305 |
| | hsa-miR-220c |
| | hsa-miR-1270 |
| | hsa-miR-1282 |
| | hsa-miR-432 |
| | hsa-miR-491-5p |
| | hsa-miR-548n |
| | hsa-miR-765 |
| | hsa-miR-768-3p |
| | hsa-miR-924 |
| HMMR | hsa-miR-936 |
| | hsa-miR-656 |
| | hsa-miR-105 |
| | hsa-miR-361-5p |
| | hsa-miR-194 |
| | hsa-miR-374a |
| | hsa-miR-590-3p |
| | hsa-miR-186 |
| | hsa-miR-769-5p |
| | hsa-miR-892a |
| | hsa-miR-380 |
| | hsa-miR-875-3p |
| | hsa-miR-208a |
| | hsa-miR-208b |
| | hsa-miR-586 |
| | hsa-miR-125a-3p |
| | hsa-miR-630 |
| | hsa-miR-374b |
| | hsa-miR-411 |
| | hsa-miR-629 |
| | hsa-miR-1286 |
| | hsa-miR-1185 |
| | hsa-miR-16 |
| | hsa-miR-200b |
| | hsa-miR-671-5p |
| | hsa-miR-95 |
| | hsa-miR-421 |
| | hsa-miR-496 |
| | hsa-miR-633 |
| | hsa-miR-1243 |
| | hsa-miR-127-5p |
| | hsa-miR-143 |
| | hsa-miR-15b |
| | hsa-miR-200c |
| | hsa-miR-24 |
| | hsa-miR-34c-3p |
| CENPF | hsa-miR-30c |
| | hsa-miR-30b |
| | hsa-miR-190 |
| | hsa-miR-508-3p |
| | hsa-miR-384 |
| | hsa-miR-512-5p |
| | hsa-miR-548p |
| | hsa-miR-297 |
| | hsa-miR-520f |
| | hsa-miR-376a |
| | hsa-miR-1184 |
| | hsa-miR-577 |
| | hsa-miR-708 |
| | hsa-miR-205 |
| | hsa-miR-376b |
| | hsa-miR-520g |

TABLE 1-continued

Gene Name and Their Associated miRNAs

| Gene | miRNA Associated with Gene |
|---|---|
| | hsa-miR-520h |
| | hsa-miR-519d |
| | hsa-miR-596 |
| | hsa-miR-768-3p |
| | hsa-miR-340 |
| | hsa-miR-620 |
| | hsa-miR-539 |
| | hsa-miR-567 |
| | hsa-miR-671-5p |
| | hsa-miR-1183 |
| | hsa-miR-129-3p |
| | hsa-miR-636 |
| | hsa-miR-106a |
| | hsa-miR-1301 |
| | hsa-miR-17 |
| | hsa-miR-20a |
| | hsa-miR-570 |
| | hsa-miR-656 |
| | hsa-miR-1263 |
| | hsa-miR-1324 |
| | hsa-miR-142-5p |
| | hsa-miR-28-5p |
| | hsa-miR-302b |
| | hsa-miR-452 |
| | hsa-miR-520d-3p |
| | hsa-miR-548o |
| | hsa-miR-892b |
| | hsa-miR-302d |
| | hsa-miR-875-3p |
| | hsa-miR-106b |
| | hsa-miR-1266 |
| | hsa-miR-1323 |
| | hsa-miR-20b |
| | hsa-miR-221 |
| | hsa-miR-520e |
| | hsa-miR-664 |
| | hsa-miR-920 |
| | hsa-miR-922 |
| | hsa-miR-93 |
| | hsa-miR-1228 |
| | hsa-miR-1271 |
| | hsa-miR-30e |
| | hsa-miR-483-3p |
| | hsa-miR-509-3-5p |
| | hsa-miR-515-3p |
| | hsa-miR-519e |
| | hsa-miR-520b |
| | hsa-miR-520c-3p |
| | hsa-miR-582-3p |
| NCAPG2 | hsa-miR-876-5p |
| | hsa-miR-1260 |
| | hsa-miR-1246 |
| | hsa-miR-548c-3p |
| | hsa-miR-1224-3p |
| | hsa-miR-619 |
| | hsa-miR-605 |
| | hsa-miR-490-5p |
| | hsa-miR-186 |
| | hsa-miR-448 |
| | hsa-miR-129-5p |
| | hsa-miR-188-3p |
| | hsa-miR-516b |
| | hsa-miR-342-3p |
| | hsa-miR-1270 |
| | hsa-miR-548k |
| | hsa-miR-654-3p |
| | hsa-miR-1290 |
| | hsa-miR-656 |
| | hsa-miR-34b |
| | hsa-miR-520g |
| | hsa-miR-1231 |
| | hsa-miR-1289 |
| | hsa-miR-1229 |
| | hsa-miR-23a |
| | hsa-miR-23b |
| | hsa-miR-616 |
| | hsa-miR-620 |
| EGFR | hsa-miR-105 |
| | hsa-miR-128a |
| | hsa-miR-128b |
| | hsa-miR-140 |
| | hsa-miR-141 |
| | hsa-miR-146a |
| | hsa-miR-146b |
| | hsa-miR-27a |
| | hsa-miR-27b |
| | hsa-miR-302a |
| | hsa-miR-302d |
| | hsa-miR-370 |
| | hsa-miR-548c |
| | hsa-miR-574 |
| | hsa-miR-587 |
| | hsa-miR-7 |
| SSTR3 | hsa-miR-125a |
| | hsa-miR-125b |
| | hsa-miR-133a |
| | hsa-miR-133b |
| | hsa-miR-136 |
| | hsa-miR-150 |
| | hsa-miR-21 |
| | hsa-miR-380-5p |
| | hsa-miR-504 |
| | hsa-miR-550 |
| | hsa-miR-671 |
| | hsa-miR-766 |
| | hsa-miR-767-3p |

Therefore, if one or more of the miRNAs in Table 1 appear in a concentration greater than 9000 copies per microliter of sample, such as a serum sample, the subject can be diagnosed with benign prostate cancer. If one or more of the miRNAs in Table 1 appear in a concentration less than 3000 copies per microliter of sample, the subject can be diagnosed with malignant prostate cancer. In some embodiments, if one or more of the miRNAs in Table 1 appear in a concentration between about 1000 to about 4500 copies per microliter of sample from a subject, a second biological sample from the subject is obtained. The second sample can be analyzed by histochemical analysis, such as by immunohistochemistry.

Furthermore, in various embodiments the micro RNAs associated with the genes for use in the methods and compositions of the invention (e.g., those overexpressed in prostate cancer) can be found in the micro RNA database online at www.microrna.org; or microrna.sanger.ac.uk/sequences, or the predicted miRNAs queried at world wide web at diana.pcbi.upenn.edu/cgi-bin/miRGen/v3/.

The miRNA that interacts with PFKFB3 can be miR-513a-3p, miR-128, miR-488, miR-539, miR-658, miR-524-5p, miR-1258, miR-150, miR-216b, miR-377, miR-135a, miR-26a, miR-548a-5p, miR-26b, miR-520d-5p, miR-224, miR-1297, miR-1197, miR-182, miR-452, miR-509-3-5p, miR-548m, miR-625, miR-509-5p, miR-1266, miR-135b, miR-190b, miR-496, miR-616, miR-621, miR-650, miR-105, miR-19a, miR-346, miR-620, miR-637, miR-651, miR-1283, miR-590-3p, miR-942, miR-1185, miR-577, miR-602, miR-1305, miR-220c, miR-1270, miR-1282, miR-432, miR-491-5p, miR-548n, miR-765, miR-768-3p or miR-924. The one or more miRNA that interacts with PFKFB3 can be detected in a sample from a subject, such as determining the copy number per microliter of the one or more miRNA, and used to characterize a cancer. The copy number per microliter of miRNA can also be used to determine whether a second biological sample from a subject should be obtained for further analysis, such as by a pathologist.

The miRNA that interacts with RHAMM can be miR-936, miR-656, miR-105, miR-361-5p, miR-194, miR-374a, miR-590-3p, miR-186, miR-769-5p, miR-892a, miR-380, miR-875-3p, miR-208a, miR-208b, miR-586, miR-125a-3p, miR-630, miR-374b, miR-411, miR-629, miR-1286, miR-1185, miR-16, miR-200b, miR-671-5p, miR-95, miR-421, miR-496, miR-633, miR-1243, miR-127-5p, miR-143, miR-15b, miR-200c, miR-24 or miR-34c-3p. The one or more miRNA that interacts with RHAMM can be detected in a sample from a subject, such as determining the copy number per microliter of the one or more miRNA, and used to characterize a cancer. The copy number per microliter of miRNA can also be used to determine whether a second biological sample from a subject should be obtained for further analysis, such as by a pathologist.

The miRNA that interacts with CENPF can be miR-30c, miR-30b, miR-190, miR-508-3p, miR-384, miR-512-5p, miR-548p, miR-297, miR-520f, miR-376a, miR-1184, miR-577, miR-708, miR-205, miR-376b, miR-520g, miR-520h, miR-519d, miR-596, miR-768-3p, miR-340, miR-620, miR-539, miR-567, miR-671-5p, miR-1183, miR-129-3p, miR-636, miR-106a, miR-1301, miR-17, miR-20a, miR-570, miR-656, miR-1263, miR-1324, miR-142-5p, miR-28-5p, miR-302b, miR-452, miR-520d-3p, miR-548o, miR-892b, miR-302d, miR-875-3p, miR-106b, miR-1266, miR-1323, miR-20b, miR-221, miR-520e, miR-664, miR-920, miR-922, miR-93, miR-1228, miR-1271, miR-30e, miR-483-3p, miR-509-3-5p, miR-515-3p, miR-519e, miR-520b, miR-520c-3p or miR-582-3p. The one or more miRNA that interacts with CENPF can be detected in a sample from a subject, such as determining the copy number per microliter of the one or more miRNA, and used to characterize a cancer. The copy number per microliter of miRNA can also be used to determine whether a second biological sample from a subject should be obtained for further analysis, such as by a pathologist.

The miRNA that interacts with NCAPG can be miR-876-5p, miR-1260, miR-1246, miR-548c-3p, miR-1224-3p, miR-619, miR-605, miR-490-5p, miR-186, miR-448, miR-129-5p, miR-188-3p, miR-516b, miR-342-3p, miR-1270, miR-548k, miR-654-3p, miR-1290, miR-656, miR-34b, miR-520g, miR-1231, miR-1289, miR-1229, miR-23a, miR-23b, miR-616 or miR-620. The one or more miRNA that interacts with NCAPG can be detected in a sample from a subject, such as determining the copy number per microliter of the one or more miRNA, and used to characterize a cancer. The copy number per microliter of miRNA can also be used to determine whether a second biological sample from a subject should be obtained for further analysis, such as by a pathologist.

The miRNA that interacts with Androgen Receptor can be miR-124a, miR-130a, miR-130b, miR-143, miR-149, miR-194, miR-29b, miR-29c, miR-301, miR-30a-5p, miR-30d, miR-30e-5p, miR-337, miR-342, miR-368, miR-488, miR-493-5p, miR-506, miR-512-5p, miR-644, miR-768-5p or miR-801. The one or more miRNA that interacts with Androgen Receptor can be detected in a sample from a subject, such as determining the copy number per microliter of the one or more miRNA, and used to characterize a cancer. The copy number per microliter of miRNA can also be used to determine whether a second biological sample from a subject should be obtained for further analysis, such as by a pathologist.

The miRNA that interacts with EGFR can be miR-105, miR-128a, miR-128b, miR-140, miR-141, miR-146a, miR-146b, miR-27a, miR-27b, miR-302a, miR-302d, miR-370, miR-548c, miR-574, miR-587 or miR-7. The one or more miRNA that interacts with EGFR can be detected in a sample from a subject, such as determining the copy number per microliter of the one or more miRNA, and used to characterize a cancer. The copy number per microliter of miRNA can also be used to determine whether a second biological sample from a subject should be obtained for further analysis, such as by a pathologist.

The miRNA that interacts with HSP90 can be miR-1, miR-513a-3p, miR-548d-3p, miR-642, miR-206, miR-450b-3p, miR-152, miR-148a, miR-148b, miR-188-3p, miR-23a, miR-23b, miR-578, miR-653, miR-1206, miR-192, miR-215, miR-181b, miR-181d, miR-223, miR-613, miR-769-3p, miR-99a, miR-100, miR-454, miR-548n, miR-640, miR-99b, miR-150, miR-181a, miR-181c, miR-522, miR-624, miR-130a, miR-130b, miR-146, miR-148a, miR-148b, miR-152, miR-181a, miR-181b, miR-181c, miR-204, miR-206, miR-211, miR-212, miR-215, miR-223, miR-23a, miR-23b, miR-301, miR-31, miR-325, miR-363, miR-566, miR-9 or miR-99b. The one or more miRNA that interacts with HSP90 can be detected in a sample from a subject, such as determining the copy number per microliter of the one or more miRNA, and used to characterize a cancer. The copy number per microliter of miRNA can also be used to determine whether a second biological sample from a subject should be obtained for further analysis, such as by a pathologist.

The miRNA that interacts with SPARC can be miR-768-5p, miR-203, miR-196a, miR-569, miR-187, miR-641, miR-1275, miR-432, miR-622, miR-296-3p, miR-646, miR-196b, miR-499-5p, miR-590-5p, miR-495, miR-625, miR-1244, miR-512-5p, miR-1206, miR-1303, miR-186, miR-302d, miR-494, miR-562, miR-573, miR-10a, miR-203, miR-204, miR-211, miR-29, miR-29b, miR-29c, miR-339, miR-433, miR-452, miR-515-5p, miR-517a, miR-517b, miR-517c, miR-592 or miR-96. The one or more miRNA that interacts with SPARC can be detected in a sample from a subject, such as determining the copy number per microliter of the one or more miRNA, and used to characterize a cancer. The copy number per microliter of miRNA can also be used to determine whether a second biological sample from a subject should be obtained for further analysis, such as by a pathologist.

The miRNA that interacts with DNMT3B can be miR-618, miR-1253, miR-765, miR-561, miR-330-5p, miR-326, miR-188, miR-203, miR-221, miR-222, miR-26a, miR-26b, miR-29a, miR-29b, miR-29c, miR-370, miR-379, miR-429, miR-519e, miR-598, miR-618 or miR-635. The one or more miRNA that interacts with DNMT3B can be detected in a sample from a subject, such as determining the copy number per microliter of the one or more miRNA, and used to characterize a cancer. The copy number per microliter of miRNA can also be used to determine whether a second biological sample from a subject should be obtained for further analysis, such as by a pathologist.

The miRNA that interacts with GART can be miR-101, miR-141, miR-144, miR-182, miR-189, miR-199a, miR-199b, miR-200a, miR-200b, miR-202, miR-203, miR-223, miR-329, miR-383, miR-429, miR-433, miR-485-5p, miR-493-5p, miR-499, miR-519a, miR-519b, miR-519c, miR-569, miR-591, miR-607, miR-627, miR-635, miR-636 or miR-659. The one or more miRNA that interacts with GART can be detected in a sample from a subject, such as determining the copy number per microliter of the one or more miRNA, and used to characterize a cancer. The copy number per microliter of miRNA can also be used to determine whether a second biological sample from a subject should be obtained for further analysis, such as by a pathologist.

The miRNA that interacts with MGMT can be miR-122a, miR-142-3p, miR-17-3p, miR-181a, miR-181b, miR-181c, miR-181d, miR-199b, miR-200a, miR-217, miR-302b, miR-32, miR-324-3p, miR-34a, miR-371, miR-425-5p, miR-496, miR-514, miR-515-3p, miR-516-3p, miR-574, miR-597, miR-603, miR-653, miR-655, miR-92, miR-92b or miR-99a. The one or more miRNA that interacts with MGMT can be detected in a sample from a subject, such as determining the copy number per microliter of the one or more miRNA, and used to characterize a cancer. The copy number per microliter of miRNA can also be used to determine whether a second biological sample from a subject should be obtained for further analysis, such as by a pathologist.

The miRNA that interacts with SSTR3 can be miR-125a, miR-125b, miR-133a, miR-133b, miR-136, miR-150, miR-21, miR-380-5p, miR-504, miR-550, miR-671, miR-766 or miR-767-3p. The one or more miRNA that interacts with SSTR3 can be detected in a sample from a subject, such as determining the copy number per microliter of the one or more miRNA, and used to characterize a cancer. The copy number per microliter of miRNA can also be used to determine whether a second biological sample from a subject should be obtained for further analysis, such as by a pathologist.

The miRNA that interacts with TOP2B can be miR-548f, miR-548a-3p, miR-548g, miR-513a-3p, miR-548c-3p, miR-101, miR-653, miR-548d-3p, miR-575, miR-297, miR-576-3p, miR-548b-3p, miR-624, miR-548n, miR-758, miR-1253, miR-1324, miR-23b, miR-320a, miR-320b, miR-1183, miR-1244, miR-23a, miR-451, miR-568, miR-1276, miR-548e, miR-590-3p, miR-1, miR-101, miR-126, miR-129, miR-136, miR-140, miR-141, miR-144, miR-147, miR-149, miR-18, miR-181b, miR-181c, miR-182, miR-184, miR-186, miR-189, miR-191, miR-19a, miR-19b, miR-200a, miR-206, miR-210, miR-218, miR-223, miR-23a, miR-23b, miR-24, miR-27a, miR-302, miR-30a, miR-31, miR-320, miR-323, miR-362, miR-374, miR-383, miR-409-3p, miR-451, miR-489, miR-493-3p, miR-514, miR-542-3p, miR-544, miR-548a, miR-548b, miR-548c, miR-548d, miR-559, miR-568, miR-575, miR-579, miR-585, miR-591, miR-598, miR-613, miR-649, miR-651, miR-758, miR-768-3p or miR-9. The one or more miRNA that interacts with TOP2B can be detected in a sample from a subject, such as determining the copy number per microliter of the one or more miRNA, and used to characterize a cancer. The copy number per microliter of miRNA can also be used to determine whether a second biological sample from a subject should be obtained for further analysis, such as by a pathologist.

In some embodiments, the one or more miRNA is selected from the group consisting of miR-498, miR-503miR-198, miR-302c, miR-345, miR-491-5p, miR-513, miR-26a-1/2, miR-375, miR-425, miR-194-1/2, miR-181a-1/2, let-7i, miR-25, miR-449, and miR-92-1/2. The one or more miR-NAs can also be selected from the group consisting of: let-7a, let-7b, let-7c, let-7d, let-7g, miR-145, miR-195, miR-199, miR-497, let-7f, miR-22, miR-30__5p, miR-490, miR-133a-1, miR-1-2, miR-218-2, miR-345, miR-410, miR-7-1/2, miR-145, miR-34a, miR-487, or let-7b. In other embodiments, the one or more miRNA is miR-99, miR-101, miR-130, miR-135, miR-141, miR-148, miR-182, miR-186, miR-206, miR-320, miR-374, miR-433, miR-496, miR-517, miR-590, miR-620, miR-768, miR-223, miR-203, miR-199, miR-519, miR-302, miR-30, miR-20, miR-200, miR-23, miR-29, miR-181, miR-548, and miR-370. The one or more miRNAs can be detected in a sample from a subject, such as determining the copy number per microliter of the one or more miRNA, and used to characterize a cancer. The copy number per microliter of miRNA can also be used to determine whether a second biological sample from a subject should be obtained for further analysis, such as by a pathologist.

In another embodiment, the one or more miRNA is miR-629, miR-671-3p, miR-9, miR-491, miR-182, miR125a-3p, miR-324-5p, miR-148b, miR-222, miR-141 or miR-370. The one or more miRNAs selected from the group consisting of: miR-629, miR-671-3p, miR-9, miR-491, miR-182, miR125a-3p, miR-324-5p, miR-148b, miR-222, and miR-141 can be used to characterize prostate cancer.

Furthermore, one or more miRNAs, such as those described in Table 1, can form a RNA patter with the mRNA of AR, PCA3, or any combination thereof, and used to characterize a cancer, such as prostate cancer. The RNA pattern can also comprise the snoRNA U50.

Assessing RNA

Assessing the RNA may be qualitative or quantitative. Assessing RNA includes detecting the RNA, such as determining the expression level (such as overexpression or underexpression as compared to a control, the presence or absence of an RNA), determining the sequence of the RNA, determining any modifications of the RNA, or detecting any mutations or variations of the RNA. The RNA level may be determined to be present or absent, greater than or less than a control, or given a numerical value for the amount of RNA, such as the copies of RNA per microliter. The expression level of an RNA can be quantified, by absolute or relative quantification. Absolute quantification may be accomplished by inclusion of known concentration(s) of one or more target nucleic acids and referencing the hybridization intensity of unknowns with the known target nucleic acids (e.g. through generation of a standard curve). Alternatively, relative quantification can be accomplished by comparison of hybridization signals between two or more genes, or between two or more treatments to quantify the changes in hybridization intensity and, by implication, transcription level.

The RNA for assessment can be is isolated from a biological sample. The RNA can be isolated from exosomes of a biological sample, such as isolated exosomes using methods as described above.

The RNA can be isolated using kits for performing membrane based RNA purification, which are commercially available. Generally, kits are available for the small-scale (30 mg or less) preparation of RNA from cells and tissues (e.g. QIAGEN RNeasy Mini kit), for the medium scale (250 mg tissue) (e.g. QIAGEN RNeasy Midi kit), and for the large scale (1 g maximum) (QIAGEN RNeasy Maxi kit). Alternatively, RNA can be isolated using the method described in U.S. Pat. No. 7,267,950, or U.S. Pat. No. 7,267,950.

The RNA or nucleic acids derived from the RNA can be used for analysis. As used herein, a nucleic acid derived from an RNA refers to a nucleic acid for whose synthesis the RNA, a mRNA transcript, or a subsequence thereof has ultimately served as a template. Thus, a cDNA reverse transcribed from a transcript, an RNA transcribed from that cDNA, a DNA amplified from the cDNA, an RNA transcribed from the amplified DNA, and the like are all derived from the transcript and detection of such derived products is indicative of the presence and/or abundance of the original transcript in a sample. Thus, suitable samples include, but are not limited to, transcripts of the gene or genes, cDNA reverse transcribed from the transcript, cRNA transcribed from the cDNA, DNA amplified from the genes, RNA transcribed from amplified DNA, and the like.

The RNA can be detected by detecting one or more labels attached to the sample RNA. The labels may be incorporated by any of a number of means well known to those of skill in the art. Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, Texas red, rhodamine, green fluorescent protein, and the like), radiolabels (e.g., 3H, 125I, 35S, 14C, or 32P), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads. Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label. For example, miRNAs can be labeled and detect, such as using a radioactive phosphate at the 5' end of the miRNA population can be used by using a polynucleotide kinase (Krichevsky A M, King K S, Donahue C P, Khrapko K, Kosik K S (2003) *RNA* 9: 1274-1281) or a radiolabeled, single nucleotide at the 3' end using RNA ligase (see for example, U.S. Pat. No. 7,541,144). Commerically available kits can also be used to label the RNA. For example, miRNA can be labeled using kits from Ambion (e.g. mirVana™ labeling kit), Exiqon (e.g. miRCURY LNA microRNA Array Hy3™/Hy5™ Power Labeling kit), Integrated DNA Technologies (e.g. miRNA StarFire Nucleic Acid Labling) Mirus Bio Corporation (e.g. LabelIT miRNA Labeling Kit) and others.

In one embodiment, after RNA has been isolated, to detect the RNA of interest, cDNA can be synthesized and either Taqman assays for specific mRNA targets can be performed according to manufacturer's protocol, or an expression microarray can be performed to look at highly multiplexed sets of expression markers in one experiment. Methods for establishing gene expression profiles include determining the amount of RNA that is produced by a gene that can code for a protein or peptide. This can be accomplished by reverse transcriptase PCR (RT-PCR), competitive RT-PCR, real time RT-PCR, differential display RT-PCR, quantitative RT-PCR, Northern Blot analysis and other related tests. These techniques can be performed using individual PCR reactions.

In some embodiments, complimentary DNA (cDNA) or complimentary RNA (cRNA) produced from mRNA is analyzed via microarray. The level of a miRNA gene product in a sample can be measured using any technique that is suitable for assessing RNA expression levels in a biological sample, including but not limited to Northern blot analysis, RT-PCR, in situ hybridization or microarray analysis. RNA detection can also be by hybridization with allele-specific probes, enzymatic mutation detection, ligation chain reaction (LCR), oligonucleotide ligation assay (OLA), flow-cytometric heteroduplex analysis, chemical cleavage of mismatches, mass spectrometry, nucleic acid sequencing, single strand conformation polymorphism (SSCP), denaturing gradient gel electrophoresis (DGGE), temperature gradient gel electrophoresis (TGGE), restriction fragment polymorphisms, serial analysis of gene expression (SAGE), or any combinations thereof.

If a quantitative result is desired, the methods disclosed herein typically use one or more controls for the relative frequencies of the amplified nucleic acids to achieve quantitative amplification. Methods of quantitative amplification are well known to those of skill in the art. For example, quantitative PCR involves simultaneously co-amplifying a known quantity of a control sequence using the same primers. This provides an internal standard that may be used to calibrate the PCR reaction. Other suitable amplification methods include, but are not limited to polymerase chain reaction (PCR) Innis, et al., PCR Protocols, A guide to Methods and Application. Academic Press, Inc. San Diego, (1990)), ligase chain reaction (LCR) (see Wu and Wallace, *Genomics*, 4: 560 (1989), Landegren, et al., *Science*, 241: 1077 (1988) and Barringer, et al., *Gene*, 89: 117 (1990)), transcription amplification (Kwoh, et al., *Proc. Natl. Acad. Sci. USA*, 86: 1173 (1989)), and self-sustained sequence replication (Guatelli, et al., *Proc. Nat. Acad. Sci. USA*, 87:1874 (1990)). Additional nucleic acid quantification methods known in the art include RT-PCR, Christmas-tree, ligase chain reaction, mass spectrometry, TMA, NASBA, branched chain reaction, and reverse transcriptase ligase chain reaction.

Additional detection and/or measurement methods include nucleic acid hybridization. Nucleic acid hybridization simply involves contacting a probe and target nucleic acid under conditions where the probe and its complementary target can form stable hybrid duplexes through complementary base pairing. As used herein, hybridization conditions refer to standard hybridization conditions under which nucleic acid molecules are used to identify similar nucleic acid molecules. Such standard conditions are disclosed, for example, in Sambrook et al., Molecular Cloning: A Laboratory Manual, Cold Spring Harbor Labs Press, 1989. Sambrook et al., ibid., is incorporated by reference herein in its entirety (see specifically, pages 9.31-9.62). In addition, formulae to calculate the appropriate hybridization and wash conditions to achieve hybridization permitting varying degrees of mismatch of nucleotides are disclosed, for example, in Meinkoth et al., 1984, Anal. Biochem. 138, 267-284; Meinkoth et al., ibid., is incorporated by reference herein in its entirety. Nucleic acids that do not form hybrid duplexes are washed away from the hybridized nucleic acids and the hybridized nucleic acids can then be detected, typically through detection of an attached detectable label. It is generally recognized that nucleic acids are denatured by increasing the temperature or decreasing the salt concentration of the buffer containing the nucleic acids. Under low stringency conditions (e.g., low temperature and/or high salt) hybrid duplexes (e.g., DNA:DNA, RNA:RNA, or RNA:DNA) will form even where the annealed sequences are not perfectly complementary. Thus specificity of hybridization is reduced at lower stringency. Conversely, at higher stringency (e.g., higher temperature or lower salt) successful hybridization requires fewer mismatches.

Nucleic acid arrays can be used to detect the one or more RNAs of a sample. The production and application of high-density arrays in gene expression monitoring have been disclosed previously in, for example, WO 97/10365; WO 92/10588; WO95/35505; U.S. Pat. Nos. 6,040,138; 5,445, 934; 5,532,128; 5,556,752; 5,242,974; 5,384,261; 5,405,783; 5,412,087; 5,424,186; 5,429,807; 5,436,327; 5,472,672; 5,527,681; 5,529,756; 5,545,531; 5,554,501; 5,561,071; 5,571,639; 5,593,839; 5,599,695; 5,624,711; 5,658,734; and 5,700,637; and Hacia et al. (1996) *Nature Genetics* 14:441-447; Lockhart et al. (1996) *Nature Biotechnol.* 14:1675-1680; and De Risi et al. (1996) *Nature Genetics* 14:457-460.

In general, in an array, an oligonucleotide, or a cDNA, genomic DNA, or fragment thereof, of a known sequence occupies a known location on a substrate. A nucleic acid sample is hybridized with an array and the amount of nucleic acids hybridized to each probe in the array is quantified. One quantifying method is to use confocal microscope and fluorescent labels. Commercially available array platform systems, such as from Affymetrix (Santa Clara, Calif.), Agilent (Santa Clara, Calif.), Atlas™ (Clontech, Mountain View, Calif.), Exiqon (Denmark) and others can be used. One can use the knowledge of the genes described herein to design novel arrays of polynucleotides, cDNAs or genomic DNAs for screening methods described herein.

In yet other embodiments, the RNA can be detected using microspheres, particles, or bead-based platforms. For example, oligonucleotides that bind and detect the RNA can be conjugated to beads. In some embodiments, commercially available platforms, such as FlexmiR™ from Luminex (Austin, Tex.), or DASL assay from Illumina (San Diego, Calif.) can be used.

Furthermore, the methods can be performed using a microfluidic device. Such systems miniaturize and compartmentalize processes that allow for binding and detection of the target RNA. In some embodiments, the RNA is also isolated from a sample in a microfluidic device. Examples of microfluidic devices that may be used are described in U.S. Pat. Nos. 7,591,936, 7,581,429, 7,579,136, 7,575,722, 7,568,399, 7,552,741, 7,544,506, 7,541,578, 7,518,726, 7,488,596, 7,485,214, 7,467,928, 7,452,713, 7,452,509, 7,449,096, 7,431,887, 7,422,725, 7,422,669, 7,419,822, 7,419,639, 7,413,709, 7,411,184, 7,402,229, 7,390,463, 7,381,471, 7,357,864, 7,351,592, 7,351,380, 7,338,637, 7,329,391, 7,323,140, 7,261,824, 7,258,837, 7,253,003, 7,238,324, 7,238,255, 7,233,865, 7,229,538, 7,201,881, 7,195,986, 7,189,581, 7,189,580, 7,189,368, 7,141,978, 7,138,062, 7,135,147, 7,125,711, 7,118,910, and 7,118,661.

In some embodiments, multiplexing can be performed. For example, multiplexing can be performed using a particle-based assay, such as bead based assay, in combination with flow cytometry. Multiparametric immunoassays or other high throughput detection assays using bead coatings with cognate ligands and reporter molecules with specific activities consistent with high sensitivity automation can be used. For example, in a particle based assay system, a binding agent for an RNA of interest, such as an oligonucleotide, can be immobilized on addressable beads or microspheres. Each binding agent for each individual binding assay (such as an immunoassay when the binding agent is an antibody) can be coupled to a distinct type of microsphere (i.e., microbead) and the binding assay reaction takes place on the surface of the microspheres. Microspheres can be distinguished by different labels, for example, a microsphere with a specific binding agent would have a different signaling label as compared to another microsphere with a different binding agent. For example, microspheres can be dyed with discrete fluorescence intensities such that the fluorescence intensity of a microsphere with a specific binding agent is different than that of another microsphere with a different binding agent.

The methods of RNA detection can be used to determine the levels of RNA in a sample, such as the mean number of copies per microliter of serum. In some embodiments, the level of each of the RNAs is calculated with a 95% confidence interval about the mean (e.g., 15,648 of +/−10,431 copies per microliter). In other embodiments, the level of each of the RNAs is calculated with an 80, 81, 82, 83, 84, 85, 86, 87, 88, 89, 90, 91, 92, 93, or 94% confidence interval. In yet other embodiments, the level of each of the RNAs is calculated with a 95, 96, 97, 98, 99 or 100% confidence interval about the mean.

RNA Patterns and PSA/PCA3 Levels

One or more RNAs can be assessed with one or more non-RNA biomarkers to characterize a cancer. A single sample can be used for assessing one or more RNAs, such as detecting one or more miRNAs, detecting one or more mRNAs, and detecting one or more non-RNA biomarkers. In some embodiments, more than one sample is used. For example, a single sample, such as blood or urine, can be used for detecting one or more miRNAs, PSA mRNA, PCA3 mRNA, and PSA protein.

A combination of an RNA level and a protein level can be used to characterize a cancer. In some embodiments, a combination of the expression level of a miRNA and a mRNA is used. For example, the mRNA level can be a of a gene or fusion gene, such as TMPRSS2:ERG or TMPRSS2:ETS. In other embodiments, the mRNA is of PCA or PCA3. In yet other embodiments, the expression levels of one or more miRNA, one or more mRNA, one or more proteins, or any combination thereof, is used to characterize a cancer. In yet other embodiments, the expression levels of one or more miRNA, one or more mRNA, one or more proteins, or any combination thereof, is determined for a first sample from a subject, such as urine or blood sample, and used to determine whether a second sample should be obtained from the subject for further analysis. For example, the second sample can be a biopsy.

For example, the expression level of one or more RNAs and of PSA protein can be used to characterize a prostate cancer. The expression level of one or more RNAs and of PSA protein can be determined in a first sample and used to determine whether a second sample, such as a biopsy, should be obtained for further analysis, such as for a histological examination. Assessing an RNA pattern and a PSA protein level can provide increased specificity or sensitivity in the characterization of prostate cancer, as compared to assessing the one or more RNAs alone or PSA protein levels alone. For example, the sensitivity, or specificity may be at least about 5, 10, 15, 20, 30, 35, 40, 50, 75, 100, 150, 200, 250, 500, 1000% or more than detection with the one or more RNAs alone or PSA protein level alone.

In some embodiments, a PCA3 level is used to characterize prostate cancer or determine whether a second sample, such as a biopsy, should be obtained for analysis. For example, in some embodiments, a miRNA level and a PCA3 mRNA level are used. Assessing a miRNA level and PCA3 mRNA level can provide increased specificity or sensitivity in the characterization of prostate cancer, as compared to assessing the miRNA level alone or the PCA3 mRNA level alone. For example, the sensitivity or specificity may be at least about 5, 10, 15, 20, 30, 35, 40, 50, 75, 100, 150, 200, 250, 500, 1000% or more.

In yet other embodiments, a miRNA level, PCA3 mRNA level, and PSA mRNA level are used to characterize prostate cancer or determine whether a second sample, such as a biopsy, should be obtained for analysis. Assessing a miRNA level, PCA3 mRNA level, and PSA mRNA levels can provide increased specificity or sensitivity in the characterization of prostate cancer, as compared to assessing 1 or 2 of the following: miRNA level, PCA3 mRNA level, and PSA mRNA level. For example, the sensitivity or specificity may be at least about 5, 10, 15, 20, 30, 35, 40, 50, 75, 100, 150, 200, 250, 500, 1000% or more.

In yet other embodiments, a miRNA level, PCA3 mRNA level, PSA mRNA level, and PSA protein level are used to characterize prostate cancer or determine whether a second sample, such as a biopsy, should be obtained for analysis. Assessing a miRNA level, PCA3 mRNA level, and PSA mRNA level can provide increased specificity or sensitivity in the characterization of a prostate cancer, as compared to assessing 1, 2, or 3 of the following: miRNA level, PCA3 mRNA level, PSA mRNA level, and PSA protein level. For example, the sensitivity or specificity may be at least about 5, 10, 15, 20, 30, 35, 40, 50, 75, 100, 150, 200, 250, 500, 1000% or more.

In some embodiments, the PCA3 mRNA level and PSA mRNA level are used to create a PCA3 score, which is a ratio of PCA3 mRNA level to PSA mRNA level, such as PCA3 mRNA copy number compared to PSA mRNA copy numbers. The PCA3 score can be used to characterize a prostate cancer or determine whether a second sample, such as a biopsy, should be obtained for analysis.

In some embodiments, the PCA3 score is used with the expression level of one or more RNAs, such as the level of a miRNA, to characterize a prostate cancer or determine whether a second sample, such as a biopsy, should be obtained for analysis. Assessing an RNA pattern and PCA3 score can provide increased specificity or sensitivity in the characterization of prostate cancer, as compared to assessing the one or more RNAs alone or PCA3 score alone. For example, the sensitivity, or specificity may be at least about 5, 10, 15, 20, 30, 35, 40, 50, 75, 100, 150, 200, 250, 500, 1000% or more.

In yet other embodiments, the PCA3 score is used with the expression level of one or more RNA and PSA protein to characterize a prostate cancer or determine whether a second sample, such as a biopsy, should be obtained for analysis. Assessing one or more RNAs and PSA protein and determining a PCA3 score can provide increased specificity or sensitivity in the characterization of prostate cancer, as compared to assessing 1 or 2 of the following: an RNA pattern, PSA protein level, and PCA3 score. For example, the sensitivity, or specificity may be at least about 5, 10, 15, 20, 30, 35, 40, 50, 75, 100, 150, 200, 250, 500, 1000% or more.

In yet other embodiments, prostate cancer is characterized by determining a product value by multiplying the level of an RNA with the level of PSA. The product value can then be used to characterize a prostate cancer. The product value can be used to diagnose a subject, to classify a cancer as benign or malignant, or to select a therapy for the subject. The product value for a subject can be compared to a reference value to characterize the cancer. For example, a reference value can be determined for diagnosing prostate cancer by determining the product value for patients with prostate cancer. Reference values can also be determined for different stages or prostate cancer, or for benign prostate cancer or malignant prostate cancer. Reference values can also be determined for drug efficacy, such as by determining reference values based on patients on effective prostate cancer therapeutics.

The product value can be used to characterize a prostate cancer with at least about 70% or 75% specificity. For example, a prostate cancer can be characterized using a product value with greater than about 76, 77, 78, 79, 80, 81, 82, 83, 84, 85, 86, 87, 88, 89, 90, 91, 92, 93, 94, 95, 96, or 97% specificity. The prostate cancer can be characterized with at least about 97.1, 97.2, 97.3, 97.4, 97.5, 97.6, 97.7, 97.8, 97.8, 97.9, 98.0, 98.1, 98.2, 98.3, 98.4, 98.5, 98.6, 98.7, 98.8, 98.9, 99.0, 99.1, 998.2, 99.3, 99.4, 99.5, 99.6, 99.7, 99.8, 99.9% specificity. In yet other embodiments, the cancer can be characterized with 100% specificity.

In some embodiments, the cancer can be characterized using a product value with at least about 60% sensitivity, such as at least about 60, 65, 70, 75, 80, 81, 82, 83, 84, 85, 86, 87, 88, 89, 90, 91, 92, 93, 94, 95, 96, or 97% sensitivity. The cancer can be characterized with at least about 97.1, 97.2, 97.3, 97.4, 97.5, 97.6, 97.7, 97.8, 97.8, 97.9, 98.0, 98.1, 98.2, 98.3, 98.4, 98.5, 98.6, 98.7, 98.8, 98.9, 99.0, 99.1, 99.2, 99.3, 99.4, 99.5, 99.6, 99.7, 99.8, 99.9% sensitivity. In yet other embodiments, the cancer can be characterized with 100% sensitivity. Furthermore, the product value can be used to characterize a prostate cancer with 100% specificity and 100% sensitivity. For example, a diagnosis of prostate cancer can be provided with 100% specificity and 100% sensitivity.

The level of RNA can be the number of copies of the miRNA per microliter of a sample and the level of PSA can be the amount of protein per microliter of sample, such as ng/ml. The amount of miRNA multiplied by the amount of PSA protein in a sample can be used to determine a product value for normal subjects and for subjects with prostate cancer. Thus, reference levels can be determined for normal subjects and for subjects with prostate cancer. The product value for a sample obtained from a subject can be determined and compared to the reference levels to characterize a cancer for the subject, such as provide a diagnosis. For example, a product value can be determined by multiplying the copies per microliter of miR-141 in a serum sample by the nanogram per microliters of PSA in a serum sample (see for example, FIG. 5). If the product value is less than 1500, 1550, 1400, 1450, or 1400, a diagnosis that the subject does not have prostate cancer can be provided. Alternatively, if the product value is greater than 1500, 1600, 1700, 1800, 1900 or 2000, a diagnosis that the subject has prostate cancer can be provided. In some embodiments, if the product value is greater than about 2000, 2100, 2200, or 2300, a diagnosis that the subject has prostate cancer is provided. A prostate cancer can be classified as benign if the product value is less than 1500. Alternatively, if the product value is greater than 1500, the cancer can be classified as malignant.

The product value can be used to classify the prostate cancer or determine whether a second sample, such as a biopsy should be obtained, for analysis. For example, if the product value is less than 1500, 1200, or 1000, a biopsy would not be obtained. In other embodiments, if the product value was greater than 1500, 1700, 1800, or 2000, a biopsy would be obtained.

In another embodiment, a method to classify a prostate cancer as benign or malignant as well as to determine whether a second sample should be obtained. For example, when the PSA protein is less than about 3 ng/mL, such as at least 2.9, 2.8, 2.7, 2.6, 2.5, 2.4, 2.3, 2.2, 2.1, or 2.0 ng/mL, the miRNA is less than about 3000 copies per microliter, such as less than about 2500, 2000, 1500, 1000 or 500, and optionally, the PCA3 score is less than 35, such as less than 30, 25, or 20, the prostate cancer is classified as benign, a second sample, such as biopsy, is not obtained, or both.

In another embodiment, when the miRNA is less than about 3000 copies per microliter, such as less than about 2500, 2000, 1500, 1000 or 500, and the PCA3 score is less than 35, such as less than 30, 25, or 20, the prostate cancer is classified as benign, a second sample, such as biopsy, is not obtained, or both.

When the PSA protein is greater than about 4 ng/mL, such as at least 4.1, 4.2, 4.3, 4.4, 4.5, 4.6, 4.7, 4.8, 4.9 or 5.0 ng/mL, the miRNA is greater than about 9000 copies per microliter, such as greater than about 9500, 10,000, 15,000 or 20,000, and optionally, the PCA3 score is greater than 35, such as at least 40, 45, or 50, the prostate cancer is classified as malignant, a second sample, such as biopsy, is obtained, or both.

In another embodiment, when the miRNA is greater than about 9000 copies per microliter, such as greater than about 9500, 10,000, 15,000 or 20,000, and the PCA3 score is greater than 35, such as at least 40, 45, or 50, the prostate cancer is classified as malignant, a second sample, such as biopsy, is obtained, or both.

Detection System and Kits

Also provided is a detection system configured to determine one or more RNAs for characterizing a cancer. For example, the detection system can be configured to assess at least 2, 3, 4, 5, 6, 7, 8, 9, 10, 15, 20, 25, 30, 40, 50, 60, 70, 80, 90, 100, 1000, 2500, 5000, 7500, 10,000, 100,000, 150,000, 200,000, 250,000, 300,000, 350,000, 400,000, 450,000, 500,000, 750,000, or 1,000,000 RNAs. For example, the detection system can be configured to assess 2, 3, 4, 5, 6, 7, 8, 9, 10, 15, 20, 25, 30, 40, 50, 60, 70, 80, 90, 100, 1000, 2500, 5000, 7500, 10,000, 100,000, 150,000, 200,000, 250,000, 300,000, 350,000, 400,000, 450,000, 500,000, 750,000, 1,000,000 or more miRNAs, wherein one or more of the miRNAs are selected from Table 1. In some embodiments, the one or more miRNAs detected by the system are selected from the group consisting of: miR-629, miR-671-3p, miR-9, miR-491, miR-182, miR125a-3p, miR-324-5p, miR-148b, miR-222, miR-141. In yet other embodiments, the one or more miRNAs are selected from the group consisting of miR-99, miR-101, miR-130, miR-135, miR-141, miR-148, miR-182, miR-186, miR-206, miR-320, miR-374, miR-433, miR-496, miR-517, miR-590, miR-620, miR-768, miR-223, miR-203, miR-199, miR-519, miR-302, miR-30, miR-20, miR-200, miR-23, miR-29, miR-181, miR-548 or miR-370. The detection system can also be configured to detect the mRNA levels of PSA, PCA or both.

The detection system can be a low density detection system or a high density detection system. For example, a low density detection system can detect up to about 100, 200, 300, 400, 500, or 1000 RNA, whereas a high density detection system can detect at least about 2000, 3000, 4000, 5000, 6000, 7000, 8000, 9,000, 10,000, 15,000, 20,000, 25,000, 50,000, or 100,000 RNAs. The detection system can be specific for detecting a species of RNA, such as miRNAs. A low density detection system for miRNA can detect up to about 100, 200, 300, 400, 500, or 1000 miRNAs. A high density detection system for miRNA can detect at least about 2000, 3000, 4000, 5000, 6000, 7000, 8000, 9,000, 10,000, 15,000, 20,000, 25,000, 50,000, or 100,000 miRNAs.

The detection system can comprise a set of probes that selectively hybridizes to the one or more of the RNAs. For example, the detection system can comprise a set of probes that selectively hybridizes to at least 2, 3, 4, 5, 6, 7, 8, 9, 10, 15, 20, 25, 30, 40, 50, 60, 70, 80, 90, 100, 1000, 2500, 5000, 7500, 10,000, 100,000, 150,000, 200,000, 250,000, 300,000, 350,000, 400,000, 450,000, 500,000, 750,000, or 1,000,000 miRNAs. For example, the set of probes can selectively hybridize to or more miRNAs selected from Table 1, one or more miRNAs are selected from the group consisting of: miR-629, miR-671-3p, miR-9, miR-491, miR-182, miR125a-3p, miR-324-5p, miR-148b, miR-222, miR-141. In yet other embodiments, the one or more miRNAs are selected from the group consisting of miR-99, miR-101, miR-130, miR-135, miR-141, miR-148, miR-182, miR-186, miR-206, miR-320, miR-374, miR-433, miR-496, miR-517, miR-590, miR-620, miR-768, miR-223, miR-203, miR-199, miR-519, miR-302, miR-30, miR-20, miR-200, miR-23, miR-29, miR-181, miR-548 or miR-370. The detection system can also comprise probes for detecting the mRNA levels of PSA, PCA or both.

The detection system can be a low density detection system or a high density detection system comprising probes to detect the RNAs. For example, a low density detection system can comprise probes to detect up to about 100, 200, 300, 400, 500, or 1000 RNA, whereas a high density detection system can comprise probes to detect at least about 2000, 3000, 4000, 5000, 6000, 7000, 8000, 9,000, 10,000, 15,000, 20,000, 25,000, 50,000, or 100,000 RNAs. The probes can be specific for detecting a species of RNA, such as miRNAs, such that a low density detection system for miRNA can comprise probes for detecting up to about 100, 200, 300, 400, 500, or 1000 miRNAs. A high density detection system for miRNA can comprise probes for detecting at least about 2000, 3000, 4000, 5000, 6000, 7000, 8000, 9,000, 10,000, 15,000, 20,000, 25,000, 50,000, or 100,000 miRNAs.

The probes may be attached to a solid substrate, such as an array or bead. Alternatively, the probes are not attached. The detection system may be an array based system, a sequencing system, a PCR-based system, or a bead-based system, such as described above. The detection system may be part of a kit. Alternatively, the kit may comprise the one or more probe sets described herein. For example, the kit may comprise probes for detecting one or more of the miRNAs selected from the group consisting of: miR-629, miR-671-3p, miR-9, miR-491, miR-182, miR125a-3p, miR-324-5p, miR-148b, miR-222, or miR-141. In yet other embodiments, the one or more miRNAs are selected from the group consisting of: miR-99, miR101, miR-130, miR-135, miR-141, miR-148, miR-182, miR-186, miR-206, miR-320, miR-374, miR-433, miR-496, miR-517, miR-590, miR-620, miR-768, miR-223, miR-203, miR-199, miR-519, miR-302, miR-30, miR-20, miR-200, miR-23, miR-29, miR-181, miR-548 or miR-370. In some embodiments, the kit further comprises one or more reagents that selectively binds to PSA or PCA3. For example, the kit may comprise a reagent, such as a probe, to detect PSA protein levels or PSA mRNA levels. The kit may also comprise a reagent to detect PCA3 mRNA levels.

Computer System

Also provided herein, is a computer system for characterizing a cancer. Accordingly, FIG. 6 is a block diagram showing a representative example logic device through which a phenotype profile and report may be generated.

Figure 6:
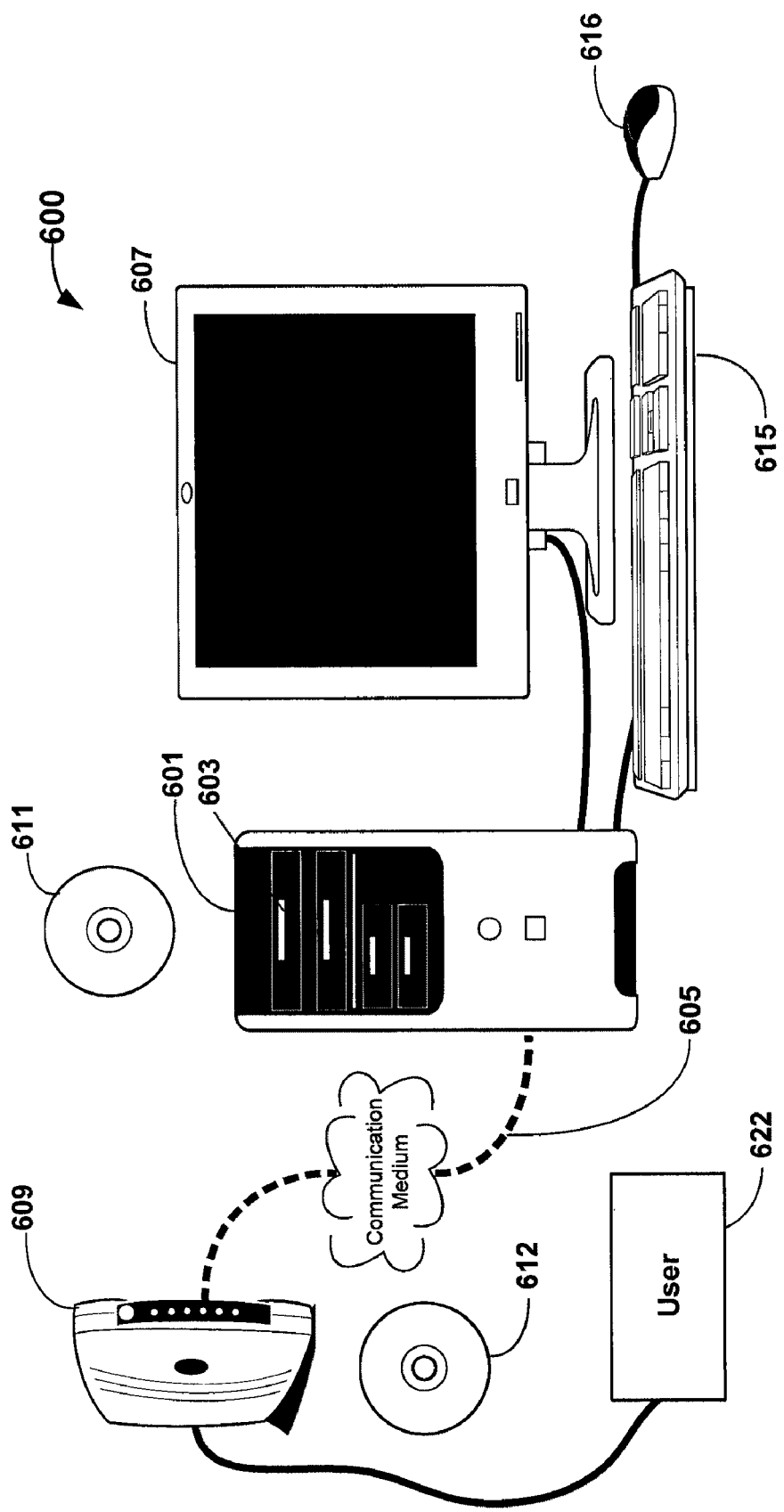
FIG. 6 is a block diagram showing a representative logic device for using with one or more methods disclosed herein, such as for receiving data, determining RNA expression levels, calculating product values, characterizing cancers, transmitting the results or data, and outputting the results.

FIG. 6 shows a computer system (or digital device) 600 to receive the expression level data from a biological sample, analyze the expression levels, determine a characteristic for a cancer (such as, but not limited to, classifying a cancer, determining whether a second sample should be obtained, providing a diagnosis, providing a prognosis, selecting a treatment, determining a drug efficacy), and produce the results, such as an output on the screen, printed out as a report, or transmitted to another computer system. The computer system 600 may be understood as a logical apparatus that can read instructions from media 611 and/or network port 605, which can optionally be connected to server 609 having fixed media 612. The system shown in FIG. 6 includes CPU 501, disk drives 603, optional input devices such as keyboard 615 and/or mouse 616 and optional monitor 607.

Data communication can be achieved through the indicated communication medium to a server 609 at a local or a remote location. The communication medium can include any means of transmitting and/or receiving data. For example, the communication medium can be a network connection, a wireless connection or an internet connection. Such a connection can provide for communication over the World Wide Web. It is envisioned that data relating to the present invention, such as the expression levels of the one or more RNAs, the results of the analysis of the expression levels (such as the characterizing or classifying of the cancer), can be transmitted over such networks or connections for reception and/or review by a party 622. The receiving party 622 can be, but is not limited, to a subject, a health care provider or a health care manager. In some embodiments, the information is stored on a computer-readable medium.

EXAMPLES

Example 1

Obtaining Serum Samples from Subjects

Blood is collected from subjects (both healthy subjects and subjects with prostate cancer) in EDTA tubes, citrate tubes or in a 10-ml Vacutainer SST plus Blood Collection Tube (BD367985 or BD366643, BD Biosciences). Blood is processed for plasma isolation within 2 h of collection.

Samples are allowed to sit at room temperature for a minimum of 30 min and a max of 2 h. Separation of the clot is accomplished by centrifugation at 1,000-1,300×g at 4° C. for 15-20 min. The serum is removed and dispensed in aliquots of 500 µl into 500-to 750-µl cryo-tubes. Specimens are stored at −80° C.

At a given sitting, the amount of blood drawn can range from ~20 to ~90 ml. Blood from several EDTA tubes is pooled and transferred to RNase/DNase-free 50-ml conical tubes (Greiner), and centrifuged at 1,200×g at room temperature in a Hettich Rotanta 460R benchtop centrifuge for 10 min. Plasma is transferred to a fresh tube, leaving behind a fixed height of 0.5 cm plasma supernatant above the pellet to avoid disturbing the pellet. Plasma is aliquoted, with inversion to mix between each aliquot, and stored at −80° C.

Example 2

RNA Isolation from Human Plasma and Serum Samples

Four hundred µl of human plasma or serum is thawed on ice and lysed with an equal volume of 2× Denaturing Solution (Ambion). RNA is isolated using the mirVana PARIS kit following the manufacturer's protocol for liquid samples (Ambion), modified such that samples are extracted twice with an equal volume of acid-phenol chloroform (as supplied by the Ambion kit). RNA is eluted with 105 µl of Ambion elution solution according to the manufacturer's protocol. The average volume of eluate recovered from each column is about 80 µl.

A scaled-up version of the mirVana PARIS (Ambion) protocol is also used: 10 ml of plasma is thawed on ice, two 5-ml aliquots are transferred to 50-ml tubes, diluted with an equal volume of mirVana PARIS 2× Denaturing Solution, mixed thoroughly by vortexing for 30 s and incubated on ice for 5 min. An equal volume (10 ml) of acid/phenol/chloroform (Ambion) is then added to each aliquot. The resulting solutions are vortexed for 1 min and spun for 5 min at 8,000 rpm, 20° C. in a JA17 rotor. The acid/phenol/chloroform extraction is repeated three times. The resulting aqueous volume is mixed thoroughly with 1.25 volumes of 100% molecular-grade ethanol and passed through a mirVana PARIS column in sequential 700-µl aliquots. The column is washed following the manufacturer's protocol, and RNA is eluted in 105 µl of elution buffer (95° C.). A total of 1.5 µl of the eluate is quantified by Nanodrop.

Example 3

Measurement of miRNA Levels in RNA from Plasma and Serum by Using TaqMan qRT-PCR Assays A fixed volume of 1.67 µl of RNA solution from about ~80 µl -eluate from RNA isolation of a given sample is used as input into the reverse transcription (RT) reaction. For samples in which RNA is isolated from a 400-µl plasma or serum sample, for example, 1.67 µl of RNA solution represents the RNA corresponding to (1.67/80)×400=8.3 µl plasma or serum. For generation of standard curves of chemically synthesized RNA oligonucleotides corresponding to known miRNAs, varying dilutions of each oligonucleotide are made in water such that the final input into the RT reaction has a volume of 1.67 µl. Input RNA is reverse transcribed using the TaqMan miRNA Reverse Transcription Kit and miRNA-specific stem-loop primers (Applied BioSystems) in a small-scale RT reaction comprised of 1.387 µl of H2O, 0.5 µl of 10× Reverse-Transcription Buffer, 0.063 µl of RNase-Inhibitor (20 units/µl), 0.05 µl of 100 mM dNTPs with dTTP, 0.33 µl of Multiscribe Reverse-Transcriptase, and 1.67 µl of input RNA; components other than the input RNA can be prepared as a larger volume master mix, using a Tetrad2 Peltier Thermal Cycler (BioRad) at 16° C. for 30 min, 42° C. for 30 min and 85° C. for 5 min. Real-time PCR is carried out on an Applied BioSystems 7900HT thermocycler at 95° C. for 10 min, followed by 40 cycles of 95° C. for 15 s and 60° C. for 1 min. Data is analyzed with SDS Relative Quantification Software version 2.2.2 (Applied BioSystems.), with the automatic Ct setting for assigning baseline and threshold for Ct determination.

The protocol can also be modified to include a preamplification step, such as for detecting miRNA. A 1.25-µl aliquot of undiluted RT product is combined with 3.75 µl of Preamplification PCR reagents [comprised, per reaction, of 2.5 µl of TaqMan PreAmp Master Mix (2×) and 1.25 µl of 0.2× TaqMan miRNA Assay (diluted in TE)] to generate a 5.0-µl preamplification PCR, which is carried out on a Tetrad2 Peltier Thermal Cycler (BioRad) by heating to 95° C. for 10 min, followed by 14 cycles of 95° C. for 15 s and 60° C. for 4 min. The preamplification PCR product is diluted (by adding 20 µl of H2O to the 5-µl preamplification reaction product), following which 2.25 µl of the diluted material is introduced into the real-time PCR and carried forward as described.

Example 4

Generation of Standard Curves for Absolute Quantification of miRNAs

Synthetic single-stranded RNA oligonucleotides corresponding to the mature miRNA sequence (miRBase Release v.10.1) are purchased from Sigma. Synthetic miRNAs are input into the RT reaction over an empirically-derived range of copies to generate standard curves for each of the miRNA TaqMan assays listed above. In general, the lower limit of accurate quantification for each assay is designated based on the minimal number of copies input into an RT reaction that results in a Ct value within the linear range of the standard curve and that is also not equivalent to or higher than a Ct obtained from an RT input of lower copy number. A line is fit to data from each dilution series using Ct values within the linear range, from which $y=m\ln(x)+b$ equations are derived for quantification of absolute miRNA copies (x) from each sample Ct (y). Absolute copies of miRNA input into the RT reaction are converted to copies of miRNA per microliter plasma (or serum) based on the knowledge that the material input into the RT reaction corresponds to RNA from 2.1% of the total starting volume of plasma [i.e., 1.67 µl of the total RNA eluate volume (80 µl on average) is input into the RT reaction]. An example of a synthetic miRNA sequence is for miR-141, 5'UAACACUGUCUGGUAAAGAUGG3' (SEQ ID NO. 1), which can be obtained commercially such as from Sigma (St. Louis, Mo.).

Example 5

Identification of Gene Expression Profiles for Prostate Cancer Using Immunohistochemistry Analysis Samples of solid tumor are excised and subjected to fixation and embedded in paraffin. The tumor block is cut into sections for placement on a glass slide. The slide is stained with the designated primary antibody which reacts with the tissue antigen as chosen by the pathologist. A labeled secondary antibody is reacted with the primary antibody and coupled to a streptavidin-horseradish peroxidase. This complex is reacted with a chromogen to produce a colored stain. The stained slides are viewed by a pathologist under a light microscope. The pathologist performs a semi-quantitative interpretation of the intensity of the staining. Typically, a 0 to 4 scale is utilized with 0 representing no staining or negative result. The pathologist then estimates the proportion of the tumor cells that are stained positively. Typically, a 0 to 100% scale is utilized. Each antibody interpretation is annotated by the pathologist into the patient report. Results of the analysis of the 22 prostate cancer samples shows the genes overexpressed in at least 10 of the 22 samples are androgen receptor, EGFR, HSP90, and SPARC (FIG. 1C).

Example 6

Tissue Preparation for Identification of Gene Expression Profiles for Prostate Cancer Tissue Preparation Before starting, and using powder-free gloves, the work area is thoroughly cleaned with either RNaseAway® (Sigma Cat. No. 83931) or 70% ethanol (70% 200proof ethanol and 30% pure water). Frozen tissue from the −80° C. freezer is removed and is immediately transferred to a tray containing dry ice, the tissue does not remain at room temperature for any length of time. Particularly if the tissue is small, as thawing could occur quickly and consequently the RNA would degrade irreversibly.

A sterile 100 mm diameter Petri dish (plastic) or tissue culture dish is placed on the clean ice to pre-chill, as well as the clean serrated tip forceps, and a new, clean heavy duty razor blade.

The tissue in the dish, if wrapped in foil or other material, is carefully unwrapped while in contact with the ice to prevent it from thawing. Even partial thawing of the tissue (which could happen is seconds) will irreversibly degrade the RNA, compromising the quality of the microarray assay or making it difficult to assay.

While using pre-chilled forceps and a razor blade, small pieces are cut off of the tissue so the sections to be used for microarray are not larger than approximately 1 mm thick. Often "shaving" off parts of the tumor is the easiest and fastest method. The forceps and razor blade are chilled every few seconds on a piece of dry ice so they remain very cold when in contact with the tissue. About 100-400 mg of tissue, roughly 20 $mm^3$, no larger than "pea-size" is used.

The tissue cuttings are carefully placed into an anti-static weight dish (preferably the "pour boat type") previously chilled on the dry ice. Then, the tissue is quickly transferred from the weigh dish to a pre-chilled borosilicate tube that has been previously marked with the appropriate specimen number, ensuring the cut tissue pieces do not stick to the walls of the tube, since they would rapidly thaw. Keeping the tube very cold and upright when transferring tissue to it is the best way to avoid that.

Any leftover tissue should be kept frozen on the dry ice until returned to a −80° C. freezer.

Homogenization Using the Covaris Tissue Processor

First, the circulating water bath (Multitemp III) is turned on, so it starts cooling off the water. Make sure the water bath contains enough water (ultrapure water only). The Covaris S-2 instrument is turned on. The water chamber of Covaris system is filled with 95% ultrapure water and 5% tap water. The computer connected to Covaris S-2 instrument is turned on, and the SonoLab software is opened.

The degassing process is turned on by clicking on the "degas" button within the SonoLab window; water should be degassed and pre-chilled (by the Multitemp III chiller water bath) for about 30 minutes, so temperature will remain between 17 and 20° C. during the homogenization of the samples. Also, the degassing process should be running during the entire session, and turned off only when ready to shut down the SonoLab software and the Covaris S-2 instrument.

The previously cut frozen tissue remains in the Covaris borosilicate tube, on the dry ice, until everything is ready for homogenization.

The program "MPI/IGC Processing" in the SonoLab program is opened. (NOTE: The following steps are done very quickly so the frozen tissue remains frozen until the last second before homogenization. The longer the tissue is thawed in between steps, the more RNA degradation typically occurs.)

Using a filtered 1000 µL pipet tip and a P-1000 pipetor, 500 µL of RLT buffer (from the Qiagen RNeasy mini kit) is added to the frozen tissue. Immediately, the screw cap is put back on and very quickly the tube is inserted into the tube holder in the Covaris S-2 instrument. 2-Mercaptoethanol is added to RLT before use. Ten µL of 2-Mercaptoethanol is added per 1 mL RLT buffer. Then the Start button to commence the homogenization is pressed.

The tube is removed after the process is completed, and is placed on wet ice. The cap is opened and 500 µL of TRIzol is added. The tube is then recapped and is quickly mixed by moving the tube side to side.

If RNA extraction is performed shortly after homogenization, the tubes remain on wet ice, otherwise all specimens are frozen in dry ice or at −80° C. until ready for RNA extraction.

When the homogenization session ends, the degassing is shut off, the water is removed from the water chamber in the Covaris S-2 instrument, then degas for about 2 seconds in order to purge the remaining water from the lines. The SonoLab program is closed first, and then the Multitemp III chiller water bath, and Covaris S-2 instrument are shut off.

Example 7

RNA Extraction and Purification for Identification of Gene Expression Profiles for Prostate Cancer TRIzol Extraction.

If the previously homogenized tissue has been stored in the −80° C. freezer, the tissue is thawed at room temperature or 65° C. Using clean powder-free gloves, the work area is cleaned again thoroughly with either RNaseAway® (Sigma Cat. No. 83931) or 70% ethanol. (NOTE: the following steps will be performed at room temperature and with room temperature reagents, unless otherwise indicated)

Tube contents are transferred to a 2 mL screw-cap, sterile and RNAse-free tube, ensuring that the lids are well tightened. The sample is heated up in a digital heat block at 65° C. for 5 minutes. If previously frozen, the sample is incubated at 65° C. for 7 minutes.

The sample is then removed from heat, and immediately, 200 µL of chloroform is added while the tubes are still hot. The caps are tightened well and are then mixed by shaking vigorously for 15-30 sec (do not vortex or DNA molecules will be sheared and may contaminate the RNA).

The tubes are then cooled on ice for 5 minutes, then the tubes are centrifuged at 10,000×g for 10 minutes at room temperature. Slowly, and using a filtered tip, approximately 0.7 mL of the upper aqueous phase which contains the total RNA is removed and is placed in a new, labeled 1.5 mL tube.

0.7 mL of room-temperature 70% ethanol is then added to the homogenized lysate, and is mixed well by pipetting.

Purification of the RNA-containing aqueous phase with RNeasy mini or micro kit. (NOTE: When processing needle biopsy samples, micro columns aree used to bind the RNA and carrier RNA added to the lysate. The RNeasy Micro kit (Qiagen Cat. No. 74004) contains poly-AN RNA to be added as carrier RNA. Before using for the first time, dissolve the carrier RNA (310 µg) in 1 mL RNase free water. Store this stock solution at −20° C., and use to make fresh dilutions for each set of RNA preps.)

To make a working solution (4 ng/µL) for 10 preps, 5 µL of the dissolved RNA is added to 34 µL of Buffer RLT and is mixed by pipetting. 6 µL of this diluted solution is added to 54 µL of Buffer RLT. The final concentration is 4 ng/µL.

Up to 0.7 mL of the sample, including any precipitate that may have formed, is applied to an RNeasy mini or micro column placed in a 2 mL collection tube. The tube is closed gently, and is centrifuged for 30 seconds at 8000×g. The remaining 0.7 mL of the sample mixture is added to the same RNeasy mini or micro column and again is centrifuged at 8000×g for 30 seconds.

0.7 mL of buffer RW1 is then added to the RNeasy mini or micro column. The tube is closed gently, and is centrifuged for 30 seconds at 8000×g to wash the column. The flow through and 2 mL collection tube is discarded.

Without touching the bottom part of the column, the RNeasy mini or micro column is transferred into a new 2 mL collection tube. 0.5 mL buffer RPE is pipetted onto the RNeasy mini or micro column. The tube is closed gently, and is centrifuged for 30 seconds at 8000×g to wash the column. The flow through is then discarded.

Again, 0.5 mL buffer RPE is added to the RNeasy column. The tube is closed gently, and is centrifuged for 2 minutes at 8000×g to dry the RNeasy silica-gel membrane. The flow through and the collection tube are then discarded.

To elute, the RNeasy mini or micro column are transferred to a new 1.5 mL collection tube (this tube is labeled with the case number). RNase free H2O (30-40 µL for a mini column or 7-14 µL for a micro column) is pipetted above the center of the RNeasy silica-gel membrane, without touching it. The tube is closed and after 2-4 minutes, the tube is centrifuged at 16,100×g for 1 minute.

The mini or micro column is then discarded and the RNA is placed on ice.

1 µL of each sample is aliquoted into a PCR tube for bio-analyzing. The RNA concentration determined by measuring the optical density or absorbance in a spectrophotometer is as follows: TE pH 8.0 is used as the diluent buffer and as the blank. A 1:100 dilution: 1 µL RNA with 99 µL TE pH 8.0 is made and the absorbance for 260 and 280 nm is read with an Agilent spectrophotometer using a quartz cuvette. The setting in the spectrophotometer is at "Ratio," and the ration obtained is the absorbance at 260 over 280, which ideally ranges from 1.8 to 2.2. In case absorbance at 260 nm is out of the linear range (below 0.1 or above 1), the dilution of the RNA in TE is repeated either by increasing the quantity of RNA or diluting it further, respectively. The RNA is then place in a designated freezer at −80° C. until ready to proceed with RNA labeling.

Example 8

RNA Amplification and Fluorescent Labeling for Identification of Gene Expression Profiles for Prostate Cancer Following RNA purification from a tissue, the amplification and labeling of this RNA is a key step in gene expression profiling using microarray analysis. This technique allows the use of purified total RNA as a template for the synthesis of complementary DNA (cDNA) by reverse transcription the first step in RNA amplification. Fluorescent complementary RNA (cRNA) is synthesized by in vitro transcription, using cDNA as a template while incorporating a nucleotide (CTP) coupled to a fluorescent cyanine dye (cyanine-3 (pink) or cyanine-5 (blue)). The resulting fluorescent RNA is then compared side by side with another RNA, labeled with a different cyanine dye, by hybridizing both to a cDNA array.

A) cDNA Synthesis from Total RNA:

Before starting, and using powder-free gloves, the work area is cleaned thoroughly with either RNaseAway® (Sigma Cat. No. 83931) or 70% ethanol (70% 200proof ethanol and 30% pure water). It is very important that the work area, the materials and equipment used are very clean, dust-and RNAse-free.

2 µg total RNA is added to a volume of 10.3 µL to a 0.2 mL microcentrifuge tube. The total concentration should be at least 5 ng/µL. When using more than 500 ng total RNA (or 10 ng or more or polyA+ RNA) the total volume should be 6.5 µL.

3 µL of T7 Promoter Primer (from kit) is then added. Nuclease-free water is then used to bring the total reaction volume to 11.5 µL. The primer and the template are denatured by incubating the reaction at 65° C. in a thermal cycler for 10 minutes. The reactions are incubated at 4° C. for 5 minutes (this can be done on ice or in the thermal cycler).

Immediately-prior to use, the following components shown in Table 2 are gently mixed by pipetting, in the order indicated, at room temperature (pre-warm the 5× First Strand Buffer by incubating the vial in an 80° C. heat block for 1-2 minutes). To ensure optimal re-suspension, vortex briefly and spin the tube briefly in a microcentrifuge at full speed to drive the contents off the walls and lid. Keep at room temperature until use.

TABLE 2

| cDNA Master Mix | | |
|---|---|---|
| Component | Vol. (µL/rxn) | Vol. (µL/6.5 rxn) |
| 5X First Strand Buffer | 4.0 | 26 |
| 0.1M DTT | 2.0 | 13 |
| 10 mM dNTP mix | 1.0 | 6.5 |
| MMLV RT | 1.0 | 6.5 |
| RNaseOUT | 0.5 | 3.3 |
| TOTAL VOLUME | 8.5 | 55.3 |

To each sample tube, 8.5 μL of the cDNA Master Mix is added. The tubes are then vortexed at a low setting with short pulses in order to avoid bubble formation. The presence of bubbles could lead to enzyme denaturation thereby impairing enzyme activity.

The samples are then incubated at 40° C. in a thermal cycler for 2 hours. The temperature of the thermocycler is then switched to 65° C. and the samples are incubated for 15 minutes (incubation at 65° C. inactivates MMLV-RT (Moloney murine leukemia virus reverse transcriptase)).

The reactions are then incubated at 4° C. for 5 minutes (this can be done on ice or in the thermal cycler). The samples are spun briefly in a microcentrifuge at full speed to drive tube contents off the tube wall and lid.

B. Fluorescent cRNA Synthesis: In Vitro Transcription and Incorporation of Cyanine 3- or Cyanine 5-CTP To each sample tube, either 2.4 μL cyanine 3-CTP (10 mM) or 2.4 μL cyanine 5-CTP (10 mM) is added. Cyanine 3 is bright pink and cyanine 5 is bright blue. Both are light sensitive and thus light exposure should be minimized. The cyanine 3-CTP (pink) is typically used for normal reference RNA labeling, and cyanine 5-CTP (blue) for the patient (tumor) RNA labeling. The 50% PEG (polyethylene glycol) solution is pre-warmed by incubating the vial in a 40° C. heat block for one minute. To ensure optimal re-suspension, vortex briefly and spin the tube briefly in a microcentrifuge at full speed to drive the contents off the tube walls and lid. The tube is kept at room temperature until use.

A Transcription Master Mix is made as shown in Table 3 Immediately-prior to use, quickly spin all tubes containing reaction components to bring down contents (for a few seconds), and combine the following components in the order indicated, at room temperature (then gently vortex Master Mix on a low setting, and spin in a microcentrifuge at full speed before adding to sample tubes). (Note: The enzymes are not added until just before performing the reaction).

TABLE 3

Transcription Master Mix

| Component | Vol.(μL/rxn) | Vol.(μL/6.5 rxn) |
|---|---|---|
| Nuclease-free water | 15.3 | 99.4 |
| 4X Transcription Buffer | 20 | 130 |
| 0.1M DTT | 6.0 | 39 |
| NTP Mix | 8.0 | 52 |
| 50% PEG | 6.4 | 41.6 |
| RNA seOUT | 0.5 | 3.3 |
| Inorganic Pyrophosphatase | 0.6 | 3.9 |
| T7 RNA Polymerase | 0.8 | 5.2 |
| TOTAL VOLUME | 57.6 | 374.4 |

To each sample tube, 57.6 μL of Transcription Master Mix is added and mixed by carefully vortexing at a low setting with short pulses in order to avoid bubble formation. The tubes are then quickly spun in a microcentrifuge at full speed to bring down contents of tube (for a few seconds).

The samples are then incubated in a thermal cycler bath at 40° C. for 2 hours.

C. Purification of Amplified cRNA (Note: Remember to add four volumes of 100% ethanol to Buffer RPE before using the kit for the first time (See bottle label for specific volume)).

20 μL of nuclease free-water is added to the cRNA sample to obtain a total volume of 100 μL. 350 μL of Buffer RLT is added and is then mixed thoroughly by gently vortexing. 250 μL of ethanol (100% purity) is added and is then mixed thoroughly by vortexing. The sample is not centrifuged after.

700 μL of the cRNA sample is added to an RNeasy mini column in a 2 mL collection tube. The sample is centrifuged for 30 seconds at 13,000×g. After this first centrifugation, color should be present in the column membrane if the labeling is successful (pink for cyanine-3 and blue for cyanine-5).

The sample is passed through the column a second time. This allows the capture of labeled RNA not retained by the membrane in the first pass. The flow-through and collection tube is then discarded.

The RNeasy column is then transferred to a new collection tube and 500 μL of buffer RPE is added to the column. The sample is then centrifuged for 30 seconds at 13,000×g. The flow through is then discarded and the collection tube is re-used.

Again, 500 μL of Buffer RPE is added to the column. The sample is then centrifuged for 1 minute at 13,000×g, and the flow through and the collection tube is discarded.

The cleaned cRNA sample is eluted by transferring the RNeasy column to a new 1.5 mL collection tube. 30 μL of RNase-free water is added directly onto the RNeasy filter membrane. After 2-3 minutes the tube is centrifuged for 30 seconds at 13,000 rpm. The flow-through and the collection tube is retained (this is the labeled cRNA; a pink (cyanine 3) or blue (cyanine 5) color should be present).

The RNA concentration is determined by measuring the optical density or absorbance in a spectrophotometer (Agilent Technologies) as follows: TE pH 8.0 is used as the diluent buffer and as the blank. A 1:20 dilution: 4 μl RNA with 76 μl TE pH 8.0 is prepared. Absorbance for 260 (RNA), 550 (cyanine 3), and 650 (cyanine 5) nm in the Agilent spectrophotometer is determined using a quartz cuvette. The setting in the spectrophotometer is at "Spectrum/Peaks" and the range is from 220 to 700 nm. The absorbance corresponding to the RNA and the cyanine dye should then be used to calculate the quantity of RNA labeled and the efficiency of the cyanine dye incorporation.

Example 8

Hybridization with the Whole Human Genome Microarray for Identification of Gene Expression Profiles for Prostate Cancer Hybridization of fluorescent complementary RNA (cRNA) to the 60-mer oligo microarray is a key step in gene expression profiling. By using Agilent microarray technology, the gene expression profile of a specimen of interest can be determined, and simultaneously compare two RNAs (i.e. tumor vs. normal) that have been previously labeled with different fluorescent dyes (cyanine 3 or cyanine 5).

Hybridization Procedure Using cRNA Labeled Targets

A) Preparation of 2× cRNA Target Solution to be Used on a 4×44K Agilent Oligo Microarray Before starting, and using powder-free gloves, the work area is cleaned thoroughly with either RNaseAway® (Sigma Cat. No. 83931) or 70% ethanol (70% 200 proof ethanol and 30% pure water). It is very important that the work area, the materials and equipment used are very clean, dust-and RNAse-free.

The 10× Blocking Agent (Agilent Cat. No. 5188-5281) is prepared (if using stock tube for the first time) by using an RNAse-free filtered pipette tip to add 0.5 mL of RNAse-free (or DEPC water) to the lyophilized pellet, mixing gently by vortexing, and centrifuging for 5-10 seconds. Once reconstituted with water, the 10× Blocking Agent should be stored frozen at −20° C. for up to 2 months.

To a 0.2 mL RNAse-free PCR tube nuclease-free water is added, bringing to 52.8 µL volume.

Using an RNAse-free filtered pipette tip, 825 ng of cyanine 3-labeled cRNA and 825 ng of cyanine 5-labeled cRNA (or more if the labeling efficiency of one of them was lower in order to add approximately equivalent quantities of cyanine dyes in both) is added.

Using an RNAse-free filtered pipette tip, 11 µL of 10× Blocking Agent is added.

This 2× Target solution may be quickly frozen in dry ice and stored in the dark in a −80° C. freezer up to 1 month.

B) cRNA Fragmentation and Preparation of 1× Hybridization Solution

To the 52.8 µL 2× cRNA Target solution, 2.2 µL of 25× Fragmentation buffer is added and is mixed gently by vortexing at a low speed before a quick centrifuge (5-10 seconds) to bring contents down from walls and tube lid.

The tube is incubated at 60° C. for 30 minutes in a thermal cycler such as the PTC-200 from MJ Research. This incubation fragments the cRNA to ideal size fragments that are optimal for hybridization. After the incubation, the tube is spun briefly in a microcentrifuge to drive the sample off the walls and lid.

55 µL of the 2× GE HI-RPM Hybridization Buffer is added and is then mixed well by careful pipetting, taking care to avoid introducing bubbles. The tube is then spun briefly in a microcentrifuge to drive the sample off the walls and lid before being used immediately.

The sample is placed on ice and is loaded onto the array as soon as possible.

C) Hybridization of Cyanine 3- and Cyanine 5-Labeled Samples to Agilent 4×44 K Oligo Microarrays As many assembled stainless steel hybridization chambers, gasket slides and microarrays as necessary to complete the microarray hybridizations are procured.

Before loading each microarray with the hybridization mixture, the samples to be assayed are written down in a numerical order by writing down the barcode number of the corresponding microarray and the position (Array 1__1, 1__2, 1__3, 1__4) where each sample was loaded.

The first gasket is placed on the base of the first hybridization chamber base, making sure that the label of the gasket slide is facing up, and that it is well placed and flush with the chamber base. 100 µL of the hybridization solution is slowly drawn up from the first sample tube avoiding any bubbles, before "dispensing and dragging" it on the center of the gasket slide, so the solution will be slowly spread with the pipet tip throughout the gasket slide while dispensing it, but leaving approximately 2-3 mm space between the solution and the gasket that surrounds it.

Once the solution is dispensed, the hybridization chamber base with the gasket slide is not moved, and the microarray is placed over it as soon as possible.

The appropriate Agilent oligo microarray is removed from its packaging using clean, powder-free gloves. To avoid damaging the microarray surface, only the area where the barcode is placed and by the ends is where the microarray should be handled (a pair of Teflon-coated, slanted tip forceps can also be helpful when handling the microarrays and placing them over the gasket slide). It also helps removing the microarray from the plastic package while the numeric side is facing up ("Agilent side is down"), since it must be placed in this direction and it is easier to confirm that the right array (with the correct barcode number) is being assigned to that sample.

The array is carefully lowered and aligned with the 4 guide posts on the chamber base. Once aligned and slightly over (and parallel to) the gasket slide, the microarray slide is gently placed against the gasket slide to complete the sandwiched slide pair. The slides are quickly assessed to assure they are completely aligned and that the oligo microarray is not ajar.

The stainless steel chamber cover is placed onto the sandwiched slides, and then the clamp assembly is slid into place, until it comes to a stopping point in the middle of the, chamber base and cover pair. The thumbscrew is tightened by turning it clockwise until it is fully handtight (without overtightening or using tools, as this may damage the parts and break the glass gasket slide and microarray.)

The chamber assembly is held vertically, and rotated slowly it clockwise 2-3 times in order to allow the hybridization solution to wet the gasket and the microarray. The sandwiched slides are inspected for bubble formation as a large mixing bubble should have formed. If stray, mixing bubbles are present and do not move as the chamber rotates, gently tap the chamber against your hand or other surface, and rotate chamber again (while in vertical position) to determine if the stationary bubbles are now moving. It is important that the stationary bubbles are dislodged before loading the assembled chamber into the hybridization rotator rack and oven.

Once all of the chambers are fully assembled, they are loaded into the hybridization rotator rack, ensuring the loaded hybridization chambers are in balance with others (can use an empty chamber as well) in the opposite position. The hybridization rotator rack is set to rotate at 10 rpm and the hybridization is at 65° C. for 17 hours.

D. Wash with Stabilization and Drying Solution.

Gene Expression Wash Buffer 2 is prewarmed to 37° C. as follows: 1000 mL of Gene Expression Wash Buffer 2 is dispensed directly into a sterile 1000-mL bottle, and is repeated until enough prewarmed Wash2 solution for the experiment is present. The 1000-mL bottle cap is tightend and placed in a 37° C. water bath the night before arrays.

Cyanine 5 is susceptible to degradation by ozone, thus, the following procedure is typically performed if the ozone levels in the laboratory exceed 5 ppb. (NOTE: Fresh Gene Expression Wash Buffer 1 and 2 should be used for each wash group (up to eight slides). The acetonitrile and Stabilization and Drying Solution may be reused for washing of up to three groups of slides.)

The Agilent Stabilization and Drying Solution contain an ozone scavenging compound dissolved in acetonitrile. The compound in solution is present in saturating amounts and may precipitate from the solution under normal storage conditions. If the solution shows visible precipitation, warming of the solution redissolves the compound. Washing slides using Stabilization and Drying Solution showing visible precipitation typically has a profound adverse effect on microarray performance.

The solution is slowly warmed in a water bath or a vented conventional oven at 40° C. in a closed container with sufficient head space to allow for expansion. If needed, the solution may be gently mixed to obtain a homogenous solution, under a vented fume hood away from open flames, or other sources of ignition. The solution is warmed only in a controlled and contained area that meets local fire code requirements.

After the precipitate is completely dissolved, the covered solution is left at room temperature, allowing it to equilibrate to room temperate prior to use. (NOTE: The original container can be used to warm the solution. The time needed to completely redissolve the precipitate is dependent on the amount of precipitate present, and may require overnight warming if precipitation is heavy. The Stabilization and Drying solution should not be filtered).

The Stabilization and Drying Solution should be set-up in a fume hood. Wash 1 and Wash 2 set-up areas should be placed close to, or preferably in, the same fume hood. Gloves and eye/face protection should be used in every step of the warming procedures.

The slide-staining dish #1 is completely filled with Gene Expression Wash Buffer 1 at room temperature. A slide rack is placed into slide-staining dish #2. A magnetic stir bar is then added and the slide-staining dish #2 is filled with enough Gene Expression Wash Buffer 1 at room temperature to cover the slide rack. This dish is placed on a magnetic stir plate.

The empty dish #3 is placed on the stir plate and a magnetic stir bar is added. The pre-warmed (37° C.) Gene Expression Wash Buffer 2 is not added until the first wash step has begun.

The slide-staining dish #4 is filled approximately three-fourths full with acetonitrile, a magnetic stir bar is added and this dish is placed on a magnetic stir plate.

The slide-staining dish #5 is filled approximately three-fourths full with Stabilization and Drying Solution, a magnetic stir bar added and this dish is placed on a magnetic stir plate.

The hybridization chamber is removed from incubator, and the hybridization chamber is prepared for disassembly. The hybridization chamber assembly is placed on a flat surface and the thumbscrew is loosened, turning counter-clockwise. The clamp assembly is slid off and the chamber cover removed.

With gloved fingers, the array-gasket sandwich is removed from the chamber base by grabbing the slides from their ends. Keeping the microarray slide numeric barcode facing up, the sandwich is quickly transferred to slide-staining dish #1.

Without letting go of the slides, the array-gasket sandwich is submerged into slide-staining dish #1 containing Gene Expression Wash Buffer 1. With the sandwich completely submerged in Gene Expression Wash Buffer 1, the sandwich is pried open from the barcode end only:

One of the blunt ends of the forceps is slipped between the slides, the forceps are turned gently upwards or downwards to separate the slides, letting the gasket slide drop to the bottom of the staining dish. The microarray slide is removed and placed into a slide rack in the slide-staining dish #2 containing Gene Expression Wash Buffer 1 at room temperature. Exposure of the slide to air should be minimized and only the barcode portion of the microarray slide or its edges should be touched.

When all slides in the group are placed into the slide rack in slide-staining dish #2, stirring is started using setting 4 for 1 minute. During this wash step, Gene Expression Wash Buffer 2 is removed from the 37° C. water bath and is poured into the Wash 2 dish. The slide rack is transferred to slide-staining dish #3 containing Gene Expression Wash Buffer 2 at elevated temperature and is stirred using setting 4 for 1 minute.

The slide rack from Gene Expression Wash Buffer 2 is removed and the rack is tilted slightly to minimize wash buffer carry-over. The slide rack is immediately transferred to the slide-staining dish #4 containing acetonitrile and is stirred using setting 4 for 30 seconds.

The slide rack is transferred to dish #5 filled with Stabilization and Drying Solution and is stirred using setting 4 for 1 minute.

The slide rack is slowly removed to minimize droplets on the slides. It should take 5 to 10 seconds to remove the slide rack. The used Gene Expression Wash Buffer 1 and Gene Expression Wash Buffer 2 are discarded.

The slides are scanned immediately to minimize the impact of environmental oxidants on signal intensities. If necessary, store slides in orange slide boxes in a N2 purge box, in the dark.

To scan the microarray slides, the scanner is turned on and after a few minutes the Agilent Scanner control is opened. The number of slides to be scanned (up to 48) is selected and after highlighting the rows that correspond to the slots to be scanned, Browse is selected and the output path or location where the image files will be saved is chosen.

To change any settings, click Settings>Modify Default Settings. A window pops up from which you can change the setting. The scanning resolution should be set up for 5 µm. The scanner reads the barcode and automatically names each file with that number.

When scanner status shows: "Scanner ready", click Scan and each array takes approximately 7 minutes to be scanned. After all scans are finished, a report will automatically appear listing all serial numbers and the status of the scan (successful or not).

The most commonly overexpressed genes are shown in FIG. 1A. In another study, the top 100 overexpressed genes were identified, and of those, the genes overexpressed in at least 5 of 6 samples were determined and is shown in FIG. 1B. An example of the results of the prostate cancer samples are shown in FIG. 2.

Example 9

Generating Product Values for Characterizing Prostate Cancer

A product value was determined by combining of miR-141 values with PSA values obtained from a subject's blood sample to create a product value used to detect prostate cancer. Data on the serum PSA levels and miR-141 levels from 25 men with metastatic prostate cancer and from 25 normal men was obtained from Mitchell et al., *PNAS* Jul. 29, 2008 Vol 105 No. 30 p. 10513-10518. The product value was determined by multiplying the miR-141 copy number by the PSA level (FIG. 5A).

The mean number of copies per microliter of serum of miR-141 from the men with prostate cancer is 15,648 with a 95% confidence interval about the mean of +/−10,431 copies per microliter. The mean number of copies per microliter of serum of miR-141 from men without prostate cancer is 560 with a 95% confidence interval of the mean of +/−223 copies per microliter (FIG. 5B). There is a clear differentiation of men with prostate cancer from normal men without prostate cancer.

The product value provides a novel analysis of data by using the number of miR-141 copies and the PSA values for a subject that is predictive of prostate cancer. The product value separates the men with prostate cancer from the men without prostate cancer with 100% sensitivity and 100% specificity.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

We claim:

1. A method of characterizing prostate cancer in a human subject comprising:
   a. determining the level of one or more proteins in a biological sample from the subject, wherein the one or more proteins comprise a protein selected from the group consisting of PSMA, EpCam, CD9, CD63, CD81, Rab-5 and a combination thereof;
   b. determining the level of miR-141 in the sample; and
   c. comparing the levels of the one or more proteins in (a) and miR-141 in (b) to a reference, wherein a difference in the levels as compared to the reference is used to characterize the prostate cancer.

2. The method of claim 1, wherein the characterizing comprises a characterization selected from the group consisting of diagnosis, prognosis, staging, grading, determination of drug efficacy, monitoring the status of the subject's response or resistance to a treatment, selection of a treatment for the prostate cancer, and a combination thereof.

3. The method of claim 2, wherein the subject is non-responsive to a current therapeutic being administered to the subject.

4. The method of claim 3, wherein the therapeutic is a cancer therapeutic.

5. The method of claim 1, wherein the reference is derived from a subject without prostate cancer.

6. The method of claim 1, wherein the reference is derived from the subject over a time course.

7. The method of claim 1, wherein the biological sample comprises a bodily fluid.

8. The method of claim 1, wherein the bodily fluid comprises a bodily fluid selected from the group consisting of peripheral blood, serum, plasma, urine, semen, prostatic fluid, cowper's fluid, pre-ejaculatory fluid, and a combination thereof.

9. The method of claim 1, wherein the bodily fluid comprises plasma or serum.

10. The method of claim 1, wherein the one or more proteins comprise CD9.

11. The method of claim 1, wherein the one or more proteins comprise CD63.

12. The method of claim 1, wherein the one or more proteins comprise CD81.

13. The method of claim 1, wherein the one or more proteins comprise PSMA.

14. The method of claim 1, wherein the one or more proteins comprise EpCam.

15. The method of claim 1, wherein the one or more proteins in (a) and miR-141 in (b) are associated with one or more membrane vesicles in the sample.

16. The method of claim 15, wherein the one or more membrane vesicles comprise membrane vesicles with a diameter of about 30 nm to about 800 nm.

17. The method of claim 15, wherein the one or more membrane vesicles comprise membrane vesicles with a diameter of about 30 nm to about 200 nm.

18. The method of claim 15, wherein the one or more membrane vesicles are isolated from the biological sample using an isolation technique selected from the group consisting of size exclusion chromatography, density gradient centrifugation, differential centrifugation, nanomembrane ultrafiltration, immunoabsorbent capture, affinity purification, microfluidic separation, and a combination thereof.

19. The method of claim 15, wherein the presence or level of CD9, CD63, and/or CD81 associated with the one or more membrane vesicles is determined.

20. The method of claim 15, wherein the one or more membrane vesicles are isolated from the biological sample using one or more binding agents for a target selected from the group consisting of PSMA, CD9, CD63, CD81, EpCam, and a combination thereof.

21. The method of claim 20, wherein the miR-141 levels are determined in the one or more isolated membrane vesicles.

22. The method of claim 15, wherein the one or more membrane vesicles are isolated from the biological sample using one or more binding agents for a target selected from the group consisting of PSA, TMPRSS2, FASLG, TNFSF10, PSMA, NGEP, I1-7RI, CSCR4, CysLT1R, TRPM8, Kv1.3, TRPV6, TRPM8, PSGR, MISIIR, galectin-3, PCA3, TMPRSS2:ERG, fragments thereof, and a combination thereof.

23. The method of claim 22, wherein the one or more binding agents comprises a binding agent selected from the group consisting of DNA molecule, RNA molecule, antibody, antibody fragment, aptamer, peptoid, zDNA, peptide nucleic acid (PNA), locked nucleic acids (LNA), lectin, peptide, dendrimer, chemical compound, and a combination thereof.

24. The method of claim 22, wherein the one or more binding agents comprises a binding agent selected from the group consisting PSA, PSMA, mAB 5D4, XPSM-A9, XPSM-A10, Galectin-3, E-selectin, Galectin-1, E4 (IgG2a kappa), and a combination thereof.

* * * * *

SEQUENCE LISTING

<160> NUMBER OF SEQ ID NOS: 1

<210> SEQ ID NO 1
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
uaacacuguc ugguaaagau gg                                              22